United States Patent
Schraga et al.

(10) Patent No.: US 10,307,095 B2
(45) Date of Patent: *Jun. 4, 2019

(54) LANCET DEVICE WITH DEPTH ADJUSTMENT AND LANCET REMOVAL SYSTEM AND METHOD

(71) Applicant: STAT MEDICAL DEVICES, INC., North Miami Beach, FL (US)

(72) Inventors: Steven Schraga, Surfside, FL (US); Brian Schwartz, Lake in the hills, IL (US); Paul R. Fuller, Danvers, MA (US)

(73) Assignee: STAT MEDICAL DEVICES, INC., North Miami Beach, FL (US)

( * ) Notice: Subject to any disclaimer, the term of this patent is extended or adjusted under 35 U.S.C. 154(b) by 283 days.

This patent is subject to a terminal disclaimer.

(21) Appl. No.: 14/866,020

(22) Filed: Sep. 25, 2015

(65) Prior Publication Data

US 2016/0007898 A1    Jan. 14, 2016

Related U.S. Application Data

(63) Continuation of application No. 12/665,600, filed as application No. PCT/US2008/067355 on Jun. 18, 2008, now Pat. No. 9,179,867.

(Continued)

(51) Int. Cl.
*A61B 5/151* (2006.01)
*A61B 5/15* (2006.01)

(52) U.S. Cl.
CPC ........ *A61B 5/15192* (2013.01); *A61B 5/1411* (2013.01); *A61B 5/1444* (2013.01);
(Continued)

(58) Field of Classification Search
CPC . A61B 5/1411; A61B 5/1444; A61B 5/15186; A61B 5/15194
(Continued)

(56) References Cited

U.S. PATENT DOCUMENTS

| 676,678 A | 6/1901 | Ellifrits |
|---|---|---|
| 1,135,465 A | 4/1915 | Pollock |

(Continued)

FOREIGN PATENT DOCUMENTS

| CA | 523 078 | 3/1956 |
|---|---|---|
| EP | 0 061 102 | 3/1982 |

(Continued)

OTHER PUBLICATIONS

Sutor et al., "Bleeding from Standardized Skin Punctures: Automated Technic for Recording Time, Intensity, and Pattern of Bleeding", A.J.C.P., vol. 55, pp. 541-549 (May 1971).

*Primary Examiner* — David C Eastwood
(74) *Attorney, Agent, or Firm* — Thomas Horstemeyer, LLP

(57) ABSTRACT

Lancet device includes a housing, a removable front cap mounted to the housing, a lancet holding member, and a trigger. A system is utilized for placing the lancet device in a trigger-set or armed position. A depth adjustment system includes a member that is at least partially rotatably mounted and that has an axis of rotation arranged substantially perpendicular to a center axis of the lancet holding member. An ejection system is utilized for at least one of preventing axial movement of the lancet holding member and removing or ejecting a lancet from the lancet holding member.

16 Claims, 25 Drawing Sheets

Related U.S. Application Data

(60) Provisional application No. 60/929,252, filed on Jun. 19, 2007.

(52) U.S. Cl.
CPC ...... *A61B 5/1513* (2013.01); *A61B 5/150022* (2013.01); *A61B 5/15113* (2013.01); *A61B 5/15117* (2013.01); *A61B 5/15186* (2013.01); *A61B 5/150198* (2013.01); *A61B 5/150412* (2013.01); *A61B 5/150503* (2013.01); *A61B 5/150824* (2013.01); *A61B 5/1405* (2013.01); *A61B 5/1519* (2013.01); *A61B 5/15194* (2013.01)

(58) Field of Classification Search
USPC .............. 606/181–183; 604/22, 117, 110, 604/207–211; 600/573, 583
See application file for complete search history.

(56) References Cited

U.S. PATENT DOCUMENTS

| | | |
|---|---|---|
| 2,699,784 A | 1/1955 | Krayl |
| 2,823,677 A | 2/1958 | Hein, Jr. |
| 2,848,809 A | 8/1958 | Crowder |
| 3,030,959 A | 4/1962 | Grunert |
| 3,589,213 A | 6/1971 | Gourley |
| 3,760,809 A | 9/1973 | Campbell, Jr. |
| 4,064,871 A | 12/1977 | Reno |
| 4,139,011 A | 2/1979 | Benoit et al. |
| 4,157,086 A | 6/1979 | Malorama et al. |
| 4,203,446 A | 5/1980 | Hofert et al. |
| 4,257,561 A | 3/1981 | McKinney |
| 4,388,925 A | 6/1983 | Burns |
| 4,426,105 A | 1/1984 | Plaquin et al. |
| 4,438,770 A | 3/1984 | Unger et al. |
| 4,449,529 A | 5/1984 | Burns et al. |
| 4,469,110 A | 9/1984 | Slama |
| 4,517,978 A | 5/1985 | Levin et al. |
| 4,527,561 A | 7/1985 | Burns |
| 4,539,988 A | 9/1985 | Shirlet et al. |
| 4,553,541 A | 11/1985 | Burns |
| 4,628,929 A | 12/1986 | Integan et al. |
| 4,643,189 A | 2/1987 | Mintz |
| 4,785,858 A | 11/1988 | Valentini et al. |
| RE32,922 E | 5/1989 | Levin et al. |
| 4,834,667 A | 5/1989 | Fowler et al. |
| 4,858,607 A | 8/1989 | Jordan et al. |
| 4,869,249 A | 9/1989 | Crossman et al. |
| 4,895,147 A | 1/1990 | Bodicky et al. |
| 4,924,879 A | 5/1990 | O'Brien |
| 4,976,724 A | 12/1990 | Nieto et al. |
| 4,990,154 A | 2/1991 | Brown et al. |
| 5,035,704 A | 7/1991 | Lambert et al. |
| 5,074,872 A | 12/1991 | Brown et al. |
| 5,133,730 A | 7/1992 | Biro et al. |
| 5,147,375 A | 9/1992 | Sullivan et al. |
| 5,201,324 A | 4/1993 | Swierczek |
| 5,212,879 A | 5/1993 | Biro et al. |
| 5,269,799 A | 12/1993 | Daniel |
| 5,282,822 A | 2/1994 | Macors et al. |
| 5,304,193 A | 4/1994 | Zhadanov |
| 5,314,441 A | 5/1994 | Cassack et al. |
| 5,324,303 A | 6/1994 | Strong et al. |
| 5,318,584 A | 7/1994 | Lange et al. |
| 5,350,392 A | 9/1994 | Purcell et al. |
| 5,356,420 A | 10/1994 | Czernecki et al. |
| 5,366,470 A | 11/1994 | Ramel |
| 5,368,047 A | 11/1994 | Suzuki et al. |
| 5,395,388 A | 3/1995 | Schraga |
| 5,423,847 A | 6/1995 | Strong et al. |
| 5,439,473 A | 8/1995 | Jorgensen |
| 5,454,828 A | 10/1995 | Schraga |
| 5,464,418 A | 11/1995 | Schraga |
| 5,476,101 A | 12/1995 | Schramm et al. |
| 5,487,748 A | 1/1996 | Marshall et al. |
| 5,509,345 A | 4/1996 | Cyktich |
| 5,518,004 A | 5/1996 | Schraga |
| 5,527,333 A | 6/1996 | Nikkels et al. |
| 5,527,334 A | 6/1996 | Kanner et al. |
| 5,529,581 A | 6/1996 | Cusack |
| 5,545,174 A | 8/1996 | Schenk et al. |
| 5,554,166 A | 9/1996 | Lange et al. |
| 5,569,286 A | 10/1996 | Peckham et al. |
| 5,569,287 A | 10/1996 | Tezuka et al. |
| 5,571,132 A | 11/1996 | Mawhirt et al. |
| D376,203 S | 12/1996 | Schraga |
| 5,613,978 A | 3/1997 | Harding |
| 5,628,764 A | 3/1997 | Schraga |
| 5,628,765 A | 3/1997 | Morita |
| 5,643,306 A | 7/1997 | Schraga |
| 5,662,672 A | 9/1997 | Pambianchi et al. |
| 5,730,753 A | 3/1998 | Morita |
| 5,733,300 A | 3/1998 | Pambianchi et al. |
| 5,741,288 A | 4/1998 | Rife |
| RE35,803 E | 5/1998 | Lange et al. |
| 5,772,677 A | 6/1998 | Mawhirt et al. |
| 5,797,940 A | 8/1998 | Mawhirt et al. |
| 5,797,942 A | 8/1998 | Schraga |
| 5,873,887 A | 2/1999 | King et al. |
| 5,879,367 A | 3/1999 | Latterell et al. |
| 5,908,434 A | 6/1999 | Schraga |
| 5,916,230 A | 6/1999 | Brenneman et al. |
| 5,971,941 A | 10/1999 | Simons et al. |
| 5,984,940 A | 11/1999 | Davis et al. |
| 6,010,519 A | 1/2000 | Mawhirt et al. |
| 6,022,366 A | 2/2000 | Schraga |
| 6,042,595 A | 3/2000 | Morita |
| 6,045,567 A | 4/2000 | Taylor et al. |
| 6,056,765 A | 5/2000 | Bajaj et al. |
| 6,071,294 A | 6/2000 | Simons et al. |
| D428,150 S | 7/2000 | Ruf et al. |
| 6,086,545 A | 7/2000 | Roe et al. |
| 6,136,013 A | 10/2000 | Marshall et al. |
| 6,152,942 A | 11/2000 | Brenneman et al. |
| 6,156,050 A | 12/2000 | Davis et al. |
| 6,156,051 A | 12/2000 | Schraga |
| 6,161,976 A | 12/2000 | Liu |
| 6,168,606 B1 | 1/2001 | Levin et al. |
| 6,183,489 B1 | 2/2001 | Douglas et al. |
| 6,190,398 B1 | 2/2001 | Schraga |
| 6,192,891 B1 | 2/2001 | Gravel et al. |
| 6,197,040 B1 * | 3/2001 | LeVaughn ........ A61B 5/150022 600/583 |
| 6,210,420 B1 | 4/2001 | Mauze et al. |
| 6,221,089 B1 | 4/2001 | Mawhirt |
| 6,228,100 B1 | 5/2001 | Schraga |
| 6,258,112 B1 | 7/2001 | Schraga |
| 6,283,982 B1 | 9/2001 | Levaughn et al. |
| 6,306,152 B1 | 10/2001 | Verdonk et al. |
| 6,322,574 B1 | 11/2001 | Lloyd et al. |
| 6,322,575 B1 | 11/2001 | Schraga |
| 6,332,871 B1 | 12/2001 | Douglas et al. |
| 6,346,114 B1 | 2/2002 | Schraga |
| 6,358,265 B1 | 3/2002 | Thorne, Jr. et al. |
| 6,364,889 B1 | 4/2002 | Kheiri et al. |
| 6,379,317 B1 | 4/2002 | Kintzig et al. |
| 6,395,495 B1 | 5/2002 | Montagnier et al. |
| 6,409,740 B1 | 6/2002 | Kuhr et al. |
| 6,419,661 B1 | 7/2002 | Kuhr et al. |
| 6,451,040 B1 | 9/2002 | Purcell |
| 6,464,649 B1 | 10/2002 | Duchon et al. |
| 6,506,168 B1 | 1/2003 | Fathallah et al. |
| 6,514,270 B1 | 2/2003 | Schraga |
| 6,530,937 B1 | 3/2003 | Schraga |
| 6,540,762 B1 | 4/2003 | Bertling |
| 6,558,402 B1 | 5/2003 | Chelak et al. |
| 6,602,268 B2 | 8/2003 | Kuhr |
| 6,645,219 B2 | 11/2003 | Roe |
| 7,087,068 B1 | 8/2006 | Marshall et al. |
| 7,175,641 B1 | 2/2007 | Schraga |
| 7,299,081 B2 | 11/2007 | Mace et al. |
| 7,311,718 B2 | 12/2007 | Schraga |

(56) References Cited

U.S. PATENT DOCUMENTS

| | | | |
|---|---|---|---|
| 9,179,867 B2* | 11/2015 | Schraga | A61B 5/1411 |
| 2001/0027327 A1 | 10/2001 | Schraga | |
| 2001/0039387 A1 | 11/2001 | Rutynowski et al. | |
| 2002/0029058 A1 | 3/2002 | Levaughn | |
| 2002/0040230 A1* | 4/2002 | Kuhr | A61B 5/15186 606/181 |
| 2002/0077650 A1 | 6/2002 | Schraga | |
| 2003/0050655 A1 | 3/2003 | Roe | |
| 2003/0050656 A1 | 3/2003 | Schraga | |
| 2003/0083686 A1 | 5/2003 | Freeman et al. | |
| 2003/0187470 A1* | 10/2003 | Chelak | A61B 5/1411 606/182 |
| 2004/0092995 A1 | 5/2004 | Boecker et al. | |
| 2004/0230216 A1 | 11/2004 | Levaughn et al. | |
| 2004/0236362 A1 | 11/2004 | Schraga | |
| 2005/0090850 A1 | 4/2005 | Thoes | |
| 2005/0118071 A1 | 6/2005 | Sacherer | |
| 2005/0234495 A1 | 10/2005 | Schraga | |
| 2005/0288699 A1 | 12/2005 | Schraga | |
| 2006/0100655 A1* | 5/2006 | Leong | A61B 5/15186 606/181 |
| 2006/0173478 A1 | 8/2006 | Schraga | |
| 2006/0200181 A1 | 9/2006 | Fukuzawa | |
| 2006/0206135 A1 | 9/2006 | Uehata | |
| 2006/0224172 A1 | 10/2006 | Levaughn et al. | |
| 2006/0241668 A1 | 10/2006 | Schraga | |
| 2006/0247670 A1 | 11/2006 | Levaughn | |
| 2006/0229652 A1 | 12/2006 | Iio et al. | |
| 2007/0083222 A1* | 4/2007 | Schraga | A61B 5/150022 606/181 |
| 2008/0033468 A1 | 2/2008 | Lathrop et al. | |
| 2008/0039885 A1 | 2/2008 | Purcell | |
| 2008/0195132 A1 | 8/2008 | Schraga | |
| 2008/0195133 A1 | 8/2008 | Zhong | |

FOREIGN PATENT DOCUMENTS

| | | |
|---|---|---|
| EP | 0 137 975 | 8/1984 |
| EP | 0 189 117 | 1/1986 |
| EP | 0 838 195 | 4/1998 |
| EP | 0 904 731 | 9/1998 |
| EP | 0 885 590 | 12/1998 |
| EP | 1 074 219 | 7/2000 |
| EP | 1 142 534 | 10/2001 |
| FR | 1 126 718 | 6/1955 |
| FR | 2 797 579 | 8/1999 |
| KR | 10-2001-0020623 | 1/2000 |
| WO | 93/19671 | 10/1993 |
| WO | 99/63897 | 12/1999 |
| WO | 03/022130 | 3/2003 |
| WO | 2005/018710 | 3/2005 |
| WO | 2006/096630 | 9/2006 |

* cited by examiner

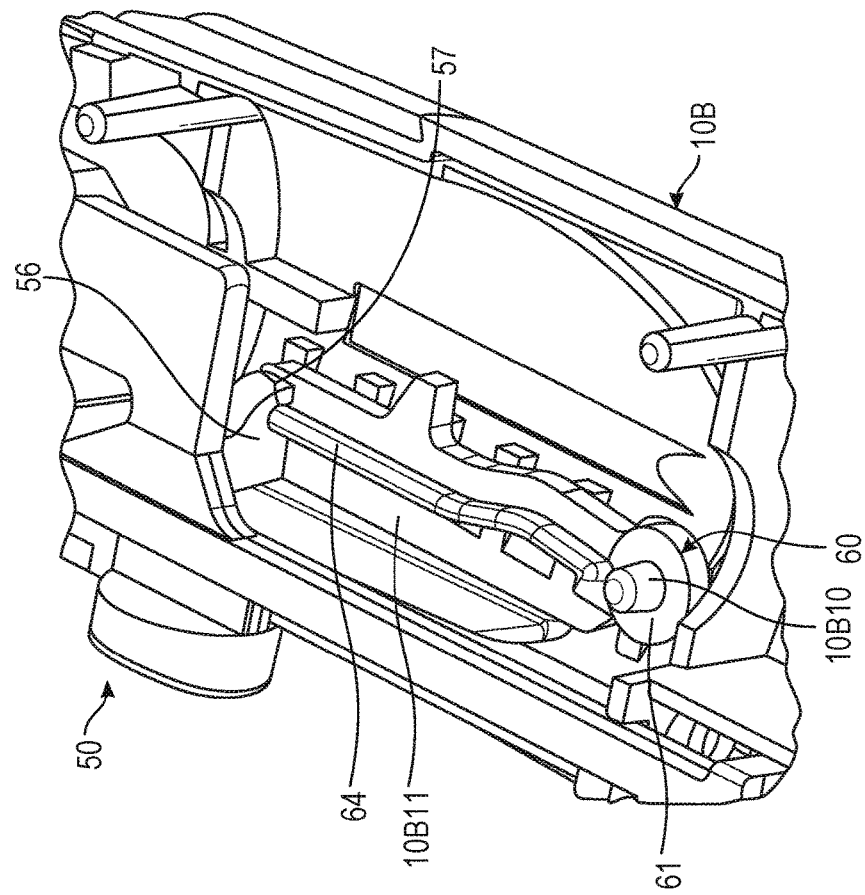
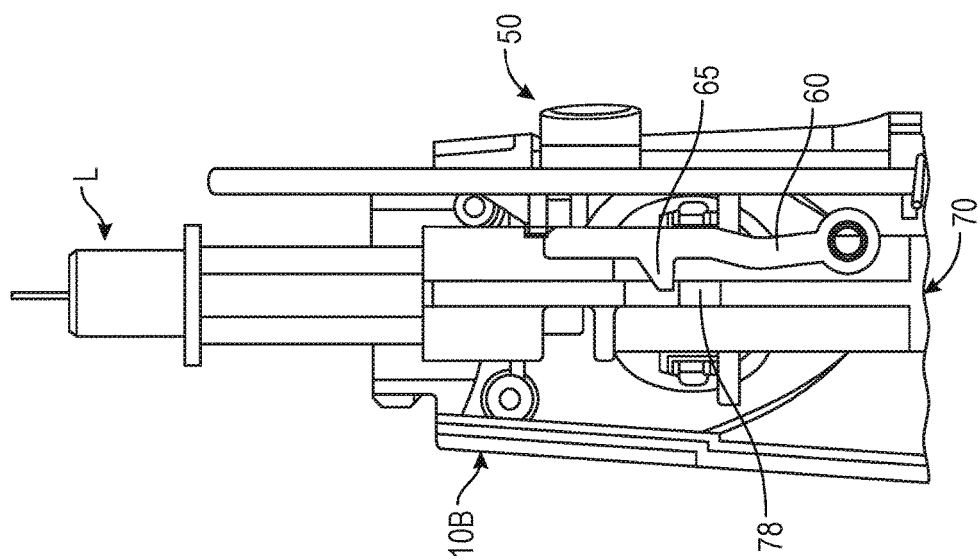

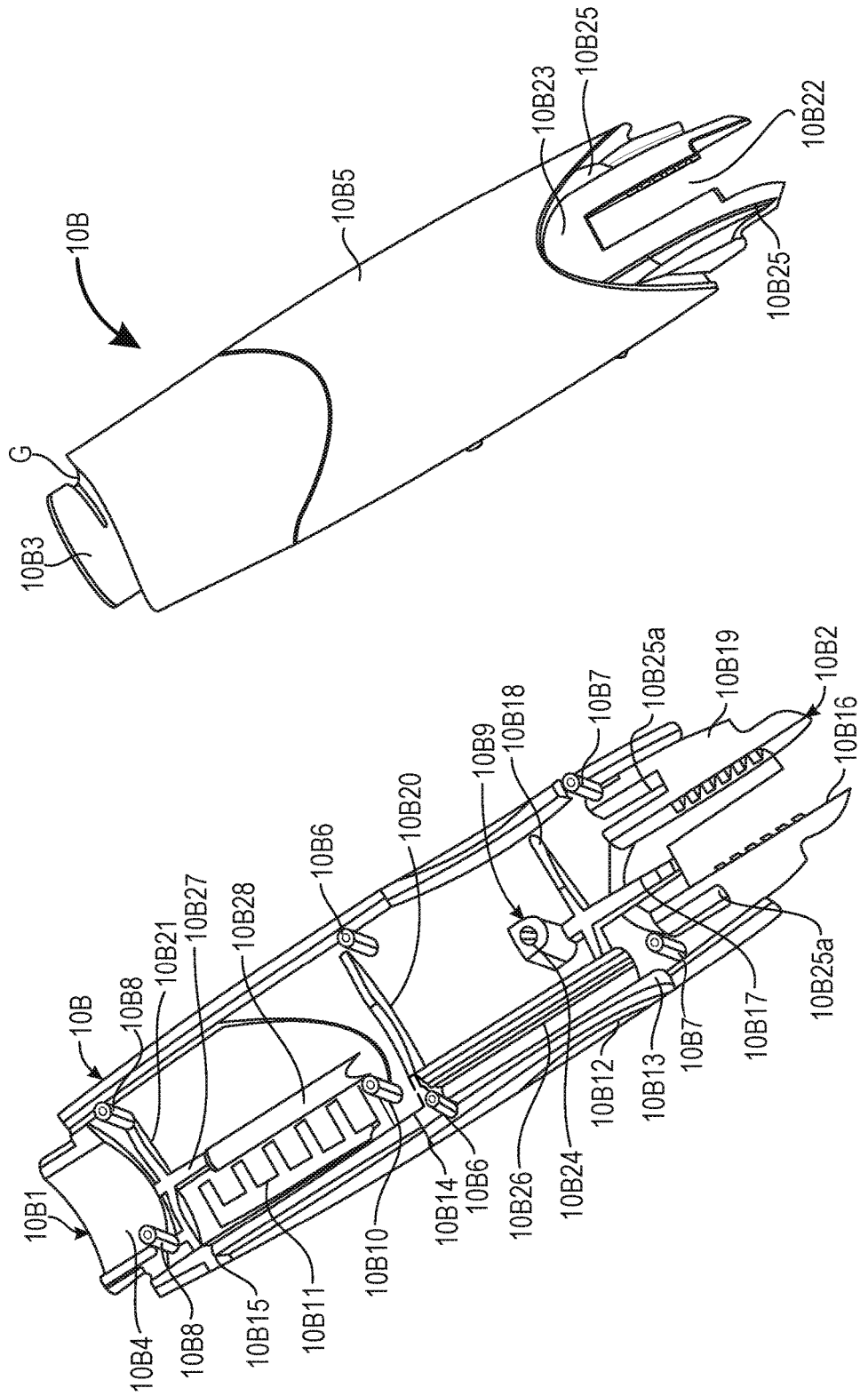

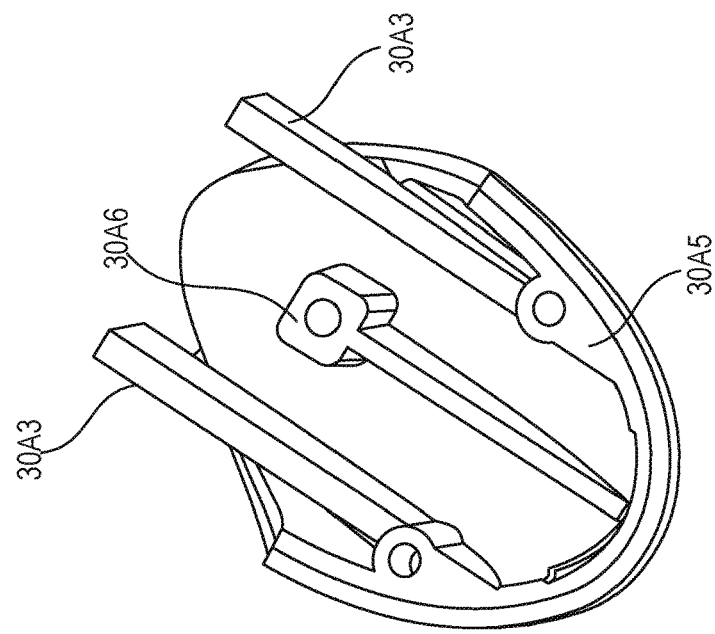
FIG. 30
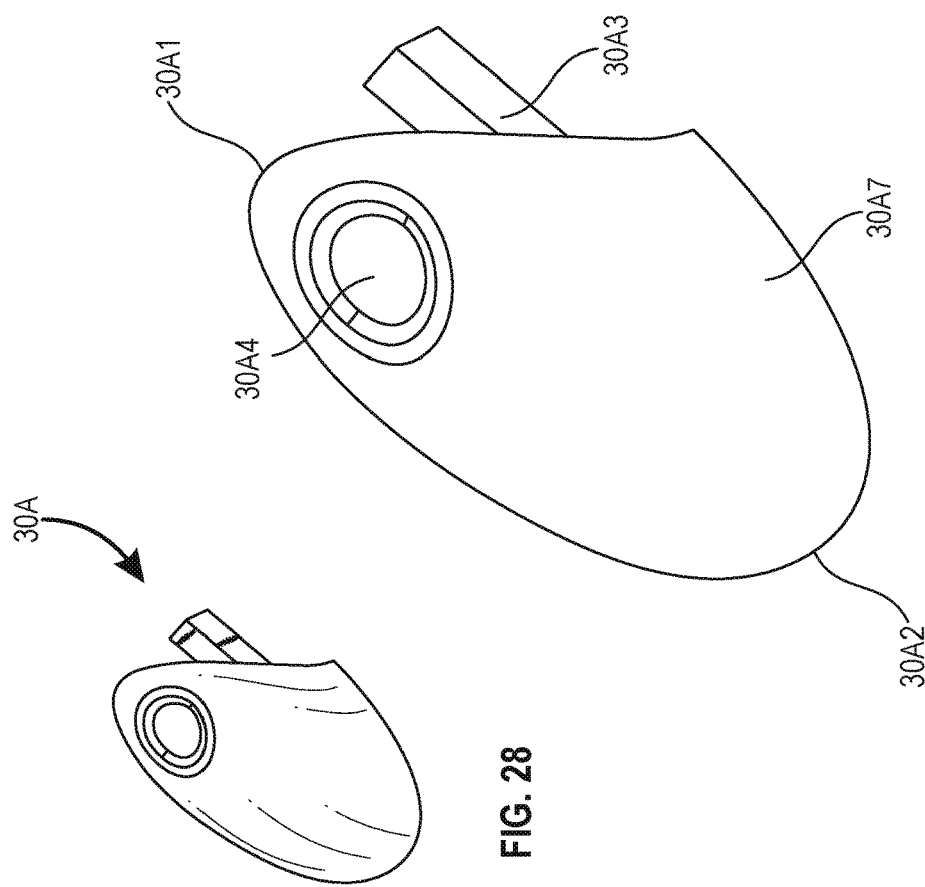
FIG. 29
FIG. 28

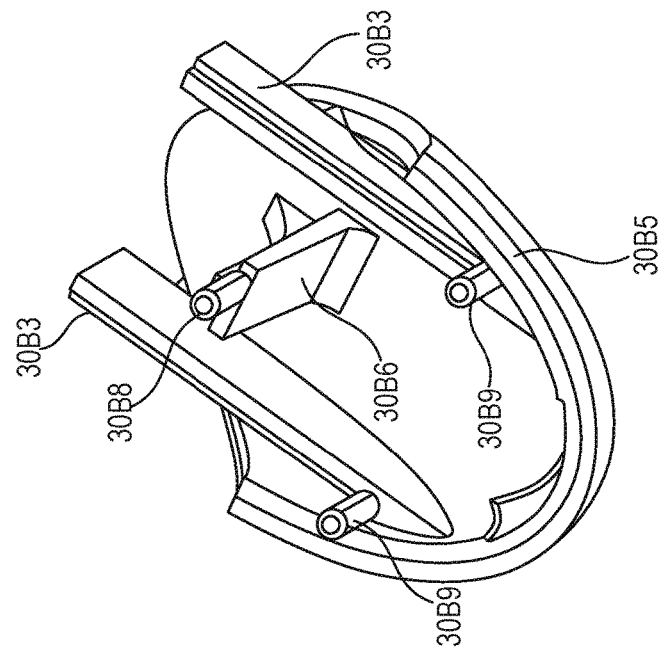
FIG. 33
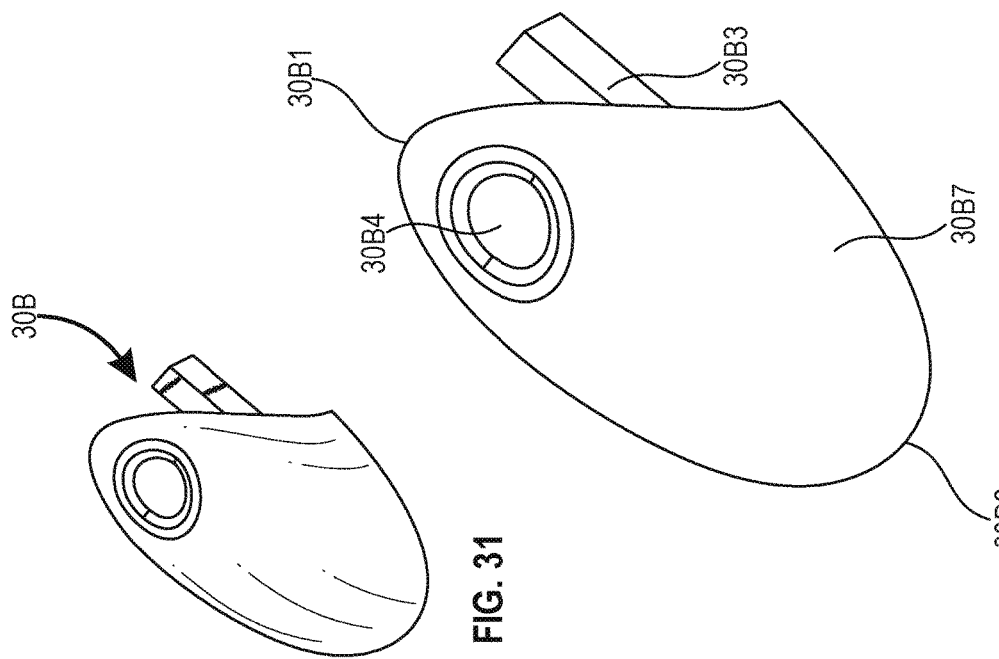
FIG. 31
FIG. 32

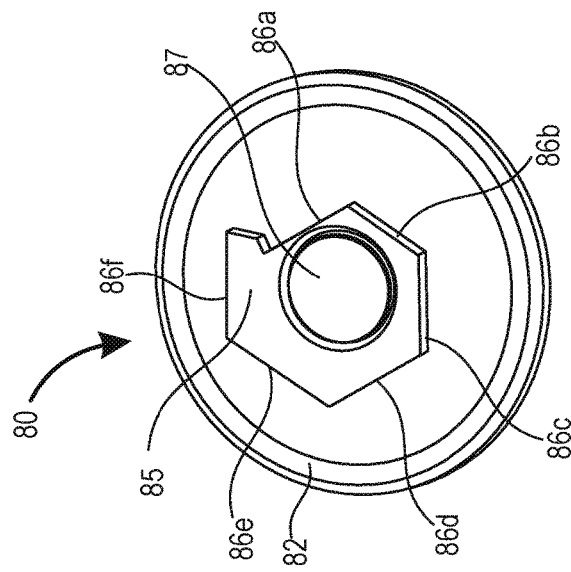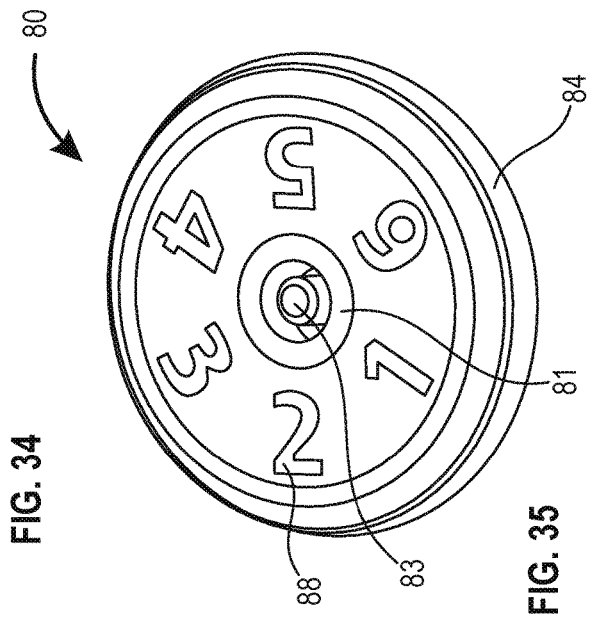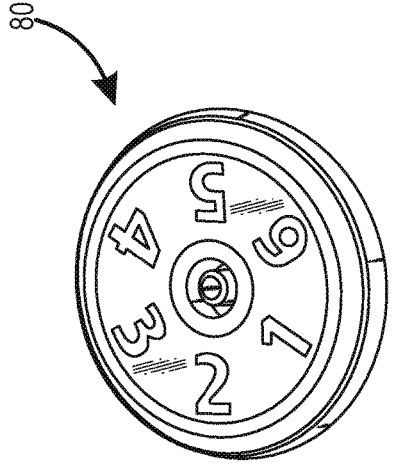

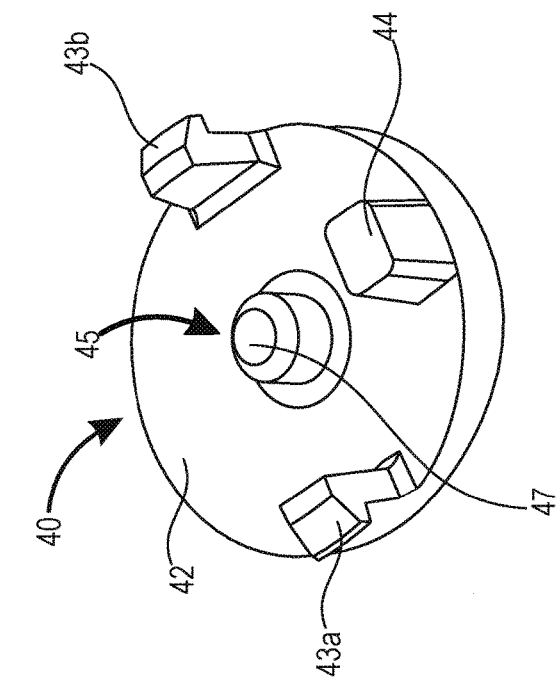
FIG. 39
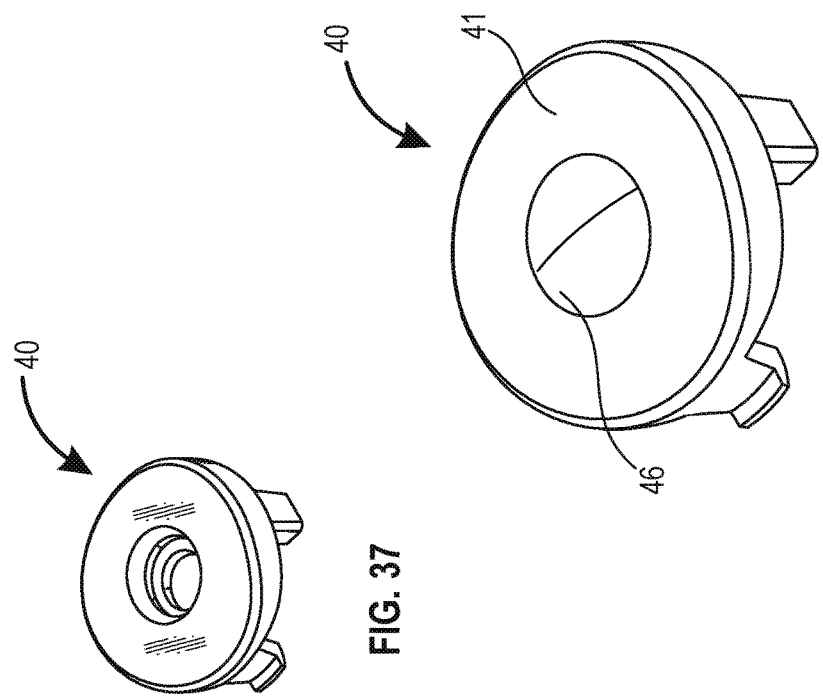
FIG. 38
FIG. 37

LANCET DEVICE WITH DEPTH ADJUSTMENT AND LANCET REMOVAL SYSTEM AND METHOD

CROSS-REFERENCE TO RELATED APPLICATIONS

The instant application is a continuation of U.S. non-provisional Application Ser. No. 12/665,600 filed on Jul. 13, 2010, which application is a U.S. National Stage of International Application No. PCT/US2008/067355 filed Jun. 18, 2008, which published as WO 2008/157610 on Dec. 24, 2008, and claims the benefit of U.S. provisional application No. 60/929,252, filed Jun. 19, 2007. The disclosures of each of these applications is hereby expressly incorporated by reference hereto in their entireties.

BACKGROUND OF THE INVENTION

1. Field of the Invention

The invention relates to a lancet device which utilizes depth adjustment and a lancet removal system. Lancet devices are used to penetrate and puncture the skin in order to allow the taking of a blood sample for testing. The present device allows the user to more safely remove and replace a lancet after each use.

2. Discussion of Background Information

Lancet devices are commonly used to prick the skin of the user so that one or more drops of blood may be extracted for testing. Some users, such as diabetics, for example, may have to test their blood sugar levels several times a day. This may be accomplished by the user using a simple needle. However, this procedure is often problematic for the user since the needle may be difficult to handle. Additionally, many users simply cannot perform the procedure owing to either a fear of needles or because they lack a steady hand. As a result, lancet devices have been developed which allow the user to more easily and reliably perform this procedure.

Most lancet devices lack convenient and flexible adjustability. Such devices are typically made adjustable by switching their tips. U.S. Pat. No. Re. 32,922 to LEVIN et al. is one such device. That is, the user must remove one tip having a set depth and replace it with another having a different set depth. This, of course, creates the problem of storing the replaceable tips, which if not properly done, may result in their misplacement, damage, contamination, or the like. Typical lancet devices also require the user to handle the lancet during replacement and installation.

An improved device would allow the user to more easily adjust the depth of penetration and would overcome some of the disadvantages described above. Moreover, since the skin thickness can vary slightly from user to user and finger to finger, a need exists for efficiently adapting the depth of penetration. For example, an index finger may be more calloused than a middle finger, and the more calloused finger will typically have thicker skin. By adjusting the depth of puncture so that the depth is no greater than necessary for extracting a required amount of blood, any pain experienced by the user may be minimized. The present device allows the user to more safely remove and replace a lancet after each use.

What is needed is a lancet device which can accurately and precisely control the depth of penetration of the needle relative to the surface of the user's skin while also being easy to use. It is also desirable for the user to be able to use and adjust the depth penetrating setting with just one hand and/or with less effort that currently required with existing lancet devices. What is also needed is a lancet device which does not require the user to handle the lancets so as to prevent inadvertent pricking of the user's skin.

SUMMARY OF THE INVENTION

According to one illustrative aspect of the invention there is provided a lancet device comprising a housing, a removable front cap mounted to the housing, a lancet holding member, a trigger, a system for placing the lancet device in a trigger-set or armed position, a depth adjustment system comprising a member that is at least partially rotatably mounted and that has an axis of rotation arranged substantially perpendicular to a center axis of the lancet holding member, and an ejection system for at least one of preventing axial movement of the lancet holding member and removing or ejecting a lancet from the lancet holding member.

The ejection system may comprise a manually activated slide button. The ejection system may each of prevent axial movement of the lancet holding member and remove or ejects the lancet from the lancet holding member.

The member that is at least partially rotatably mounted may comprise a thumbwheel having plural cam or stop surfaces. The member that is at least partially rotatably mounted may comprise a thumbwheel having indicia. The member that is at least partially rotatably mounted may comprise a thumbwheel having indicia which is visible through an opening located in the housing. The member that is at least partially rotatably mounted may comprise a thumbwheel having portions which can be gripped by a user from outside of the housing. The member that is at least partially rotatably mounted may comprise a thumbwheel having oppositely arranged portions which project outside of the housing.

The lancet device may further comprise a first spring for causing movement of the lancet holding member towards a puncturing position and a second for causing a back cap to move towards an initial position from a retracted position. The lancet device may further comprise a first spring for causing movement of the lancet holding member towards a puncturing position, a second for causing a back cap to move towards an initial position from a retracted position, and a third spring for causing a slide member of the ejection system to move towards an initial position from an extended position.

The invention also provides for a method of puncturing a surface of skin using the lancet device of the type described above, wherein the method comprises arranging the lancet device adjacent against a user's skin and triggering the lancet device so that a lancet is caused to penetrate the user's skin.

The invention also provides for a lancet device comprising a housing, a removable front cap mounted to the housing, a lancet holding member having a front end adapted to receive therein a removable lancet, a trigger, a system for placing the lancet device in a trigger-set or armed position, a depth adjustment system comprising a member having plural cam surfaces, and an ejection system for at least one of preventing axial movement of the lancet holding member, removing or ejecting a lancet from the lancet holding member, and removing or ejecting the front cap.

The ejection system may comprise a manually activated slide button. The ejection system may each of prevent axial movement of the lancet holding member, remove or eject the lancet from the lancet holding member, and remove or eject the front cap.

The member may be at least partially rotatably mounted and comprises a thumbwheel. The thumbwheel may comprise indicia. The indicia may be visible through an opening located in the housing. The thumbwheel may be one of has portions which can be gripped by a user from outside of the housing, and oppositely arranged portions which project outside of the housing.

The lancet device may further comprise a first spring for causing movement of the lancet holding member towards a puncturing position and a second for causing a back cap to move towards an initial position from a retracted position. The lancet device may further comprise a first spring for causing movement of the lancet holding member towards a puncturing position, a second for causing a back cap to move towards an initial position from a retracted position, and a third spring for causing a slide member of the ejection system to move towards an initial position from an extended position.

The invention also provides for a method of puncturing a surface of skin using the lancet device of the type described above, wherein the method comprises arranging the lancet device adjacent against a user's skin and triggering the lancet device so that a lancet is caused to penetrate the user's skin.

The invention also provides for a lancet device comprising a housing having an ergonomic shape, a removable front cap mounted to the housing, a movably mounted lancet holding member having a front end adapted to receive therein a removable lancet, a trigger arranged on a side wall of the hosing, a system for placing the lancet device in a trigger-set or armed position, a depth adjustment system comprising a member having plural cam surfaces, and an ejection system for at least one of preventing axial movement of the lancet holding member, removing or ejecting a lancet from the lancet holding member, and removing or ejecting the front cap.

The invention also provides for a lancet device of the type disclosed herein whose parts utilize the same materials as the materials of corresponding parts of U.S. Ser. No. 10/441,065 to SCHRAGA filed May 20, 2003, the disclosure of this document is hereby expressly incorporated by reference in its entirety.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 10 shows a bottom partial view of a front portion (bottom housing part removed) of the device of FIG. 1 with the front cap removed and after the lancet ejection system has been moved to a lancet ejection position;

FIG. 11 shows a top partial view of a front portion (top housing part and lancet holding member removed) of the device of FIG. 1 with the front cap removed and after the lancet ejection system has been moved to a lancet ejection position;

FIG. 24 shows a perspective inside view of the lower housing part shown in FIG. 23;

FIG. 25 shows a perspective outside view of the lower housing part shown in FIG. 23;

FIG. 28 shows a perspective rear side view of an upper portion of the back cap used in the lancet device shown in FIG. 1;

FIG. 29 shows an enlarged perspective rear side view of an upper portion of the back cap used in the lancet device shown in FIG. 1;

FIG. 30 shows a perspective inside view of the upper portion of the back cap shown in FIG. 29;

FIG. 31 shows a perspective rear side view of a lower portion of the back cap used in the lancet device shown in FIG. 1;

FIG. 32 shows an enlarged perspective rear side view of a lower portion of the back cap used in the lancet device shown in FIG. 1;

FIG. 33 shows a perspective inside view of the lower portion of the back cap shown in FIG. 32;

FIG. 34 shows a perspective front side view of the thumb wheel used in the embodiment of FIG. 1;

FIG. 35 shows an enlarged view of FIG. 34;

FIG. 36 shows a perspective rear side view of the thumb wheel shown in FIG. 35;

FIG. 37 shows a perspective front side view of the trigger used in the embodiment of FIG. 1;

FIG. 38 shows an enlarged view of FIG. 37;

FIG. 39 shows a perspective rear side view of the trigger shown in FIG. 38;

DETAILED DESCRIPTION OF THE PRESENT INVENTION

Figure 1:
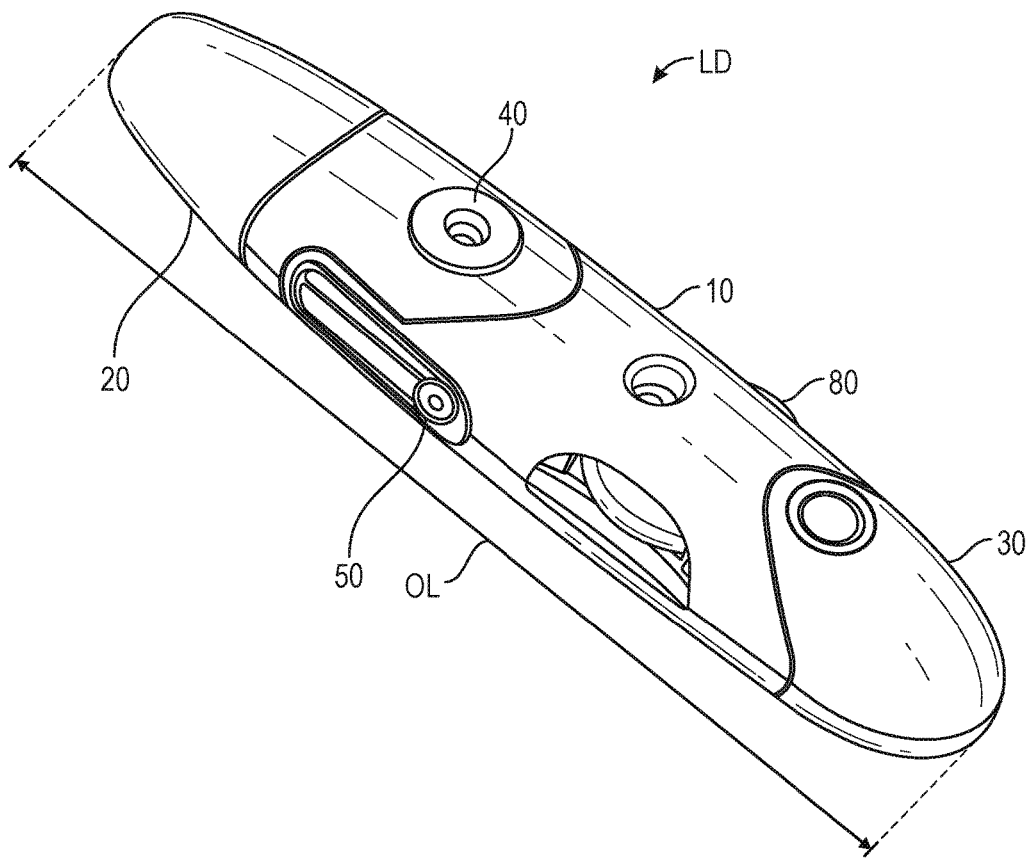
FIG. 1 shows a left front side perspective view of a non-limiting embodiment of the invention.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

FIGS. 1-49 show one non-limiting embodiment of a lancet device LD. The lancet device LD includes the following main components: a housing or body 10 which preferably comprises housing parts 10A and 10B, a front cap 20, a back cap 30 which preferably comprises parts 30A and 30B, a trigger 40, a lancet advance button or member 50, a locking member 60, a lancet holding member 70, a depth adjustment or thumb wheel member 80, and three springs S1, S2 and S3.

As can be seen in FIG. 1, the lancet device LD can preferably have, by way of non-limiting example, an overall length OL which is approximately 5 inches and an overall width or diameter (measured over the device's largest portion) of approximately 1.25 inches. The lancet device LD also preferably has an ergonomic shape such that it can be held comfortably in a user's hand such that the user can rotate (both clockwise and counterclockwise) the depth adjustment thumb wheel 80 with the user's thumb and index finger, as will be described in detail later on, to set the depth of penetration prior to use. The user can also depress and slide forward the advance button 50 in order cause a forward advance of a lancet and optionally simultaneously cause removal of the front cap 20, as will be described in detail later on. The user can also depress the trigger 40 with either the user's thumb of index finger. The only step which likely requires the user to use two hands, is the step of placing the lancet device LD is an armed or trigger-set position—which will be described in detail later on.

Figure 2:
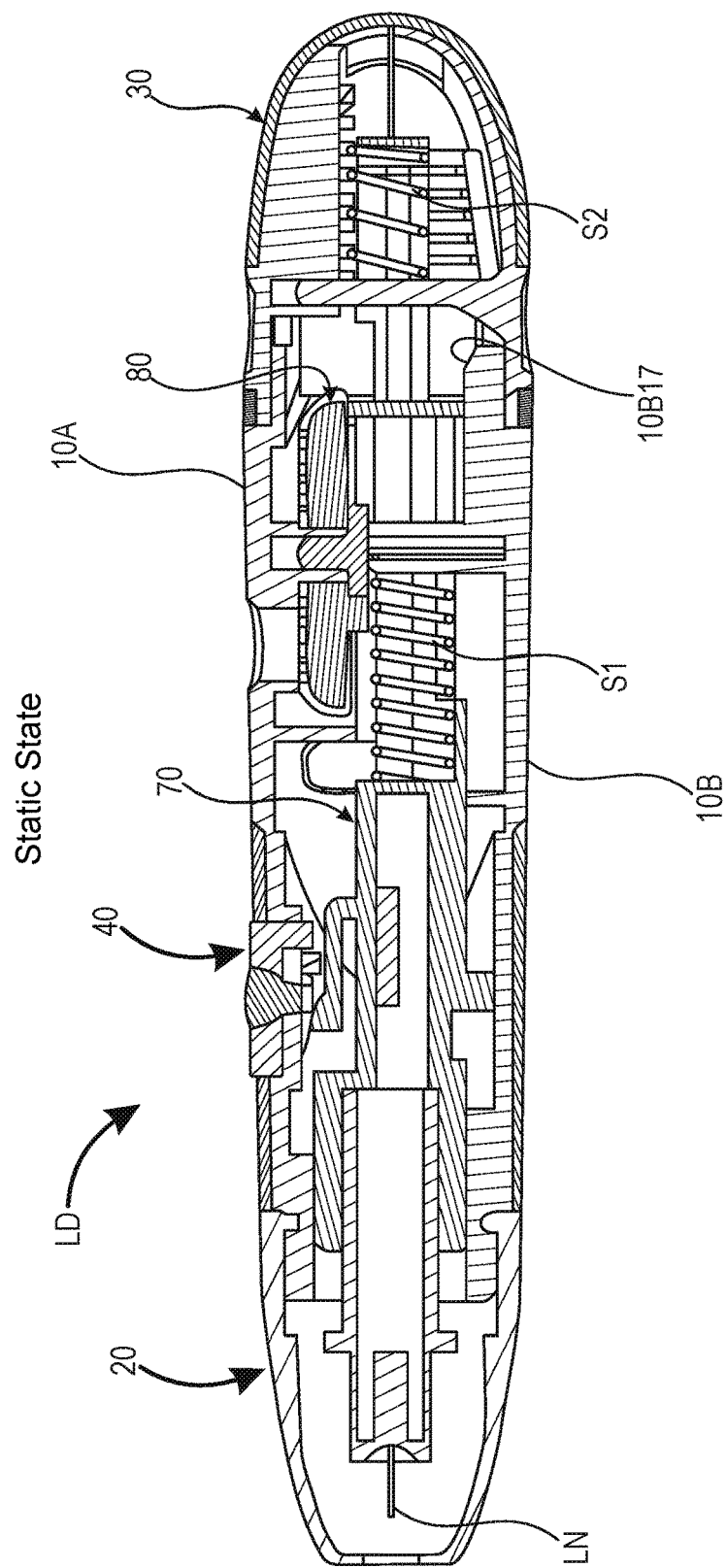
FIG. 2 shows a side cross-section view of FIG. 1. The device is shown in an initial or intermediate state.
Figure 3:
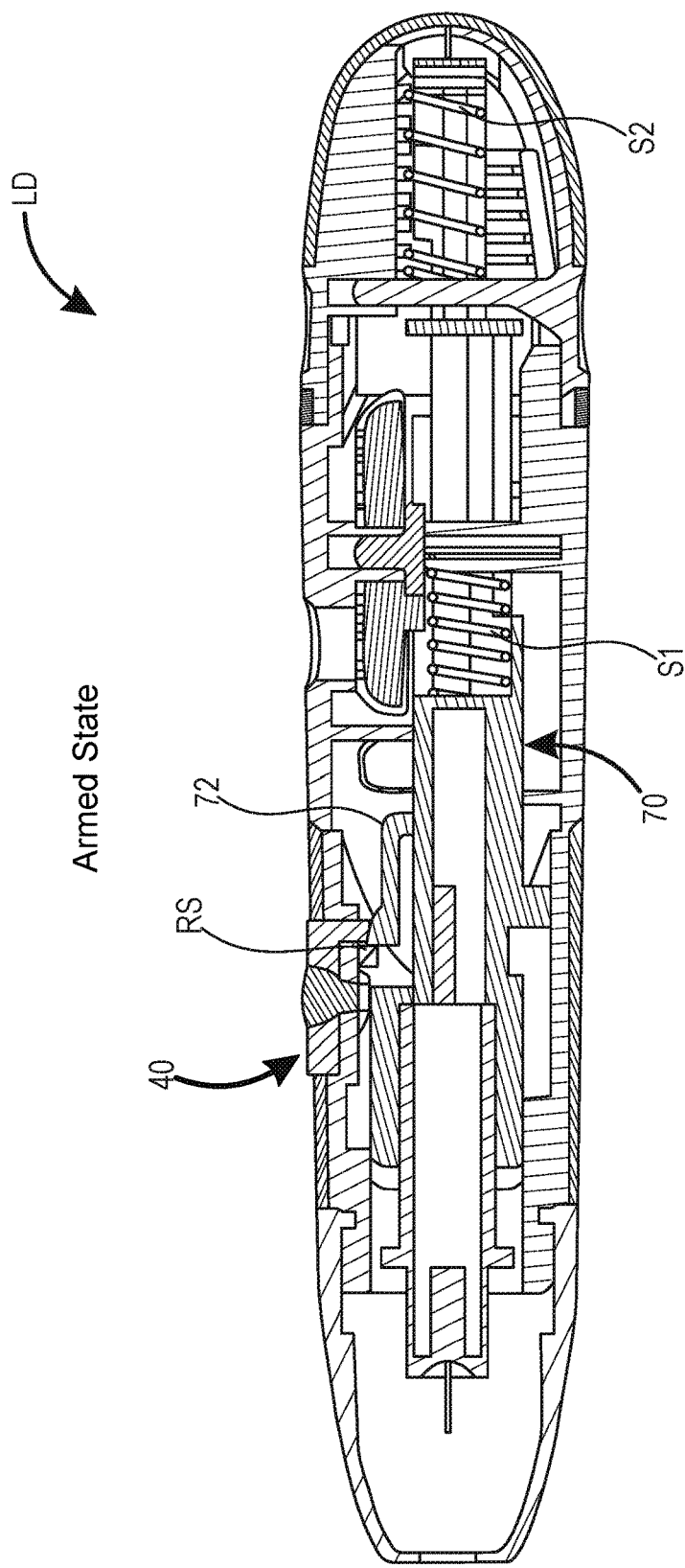
FIG. 3 shows a side cross-section view of FIG. 2 after the device is placed in an arming or trigger-set position.
Figure 4:
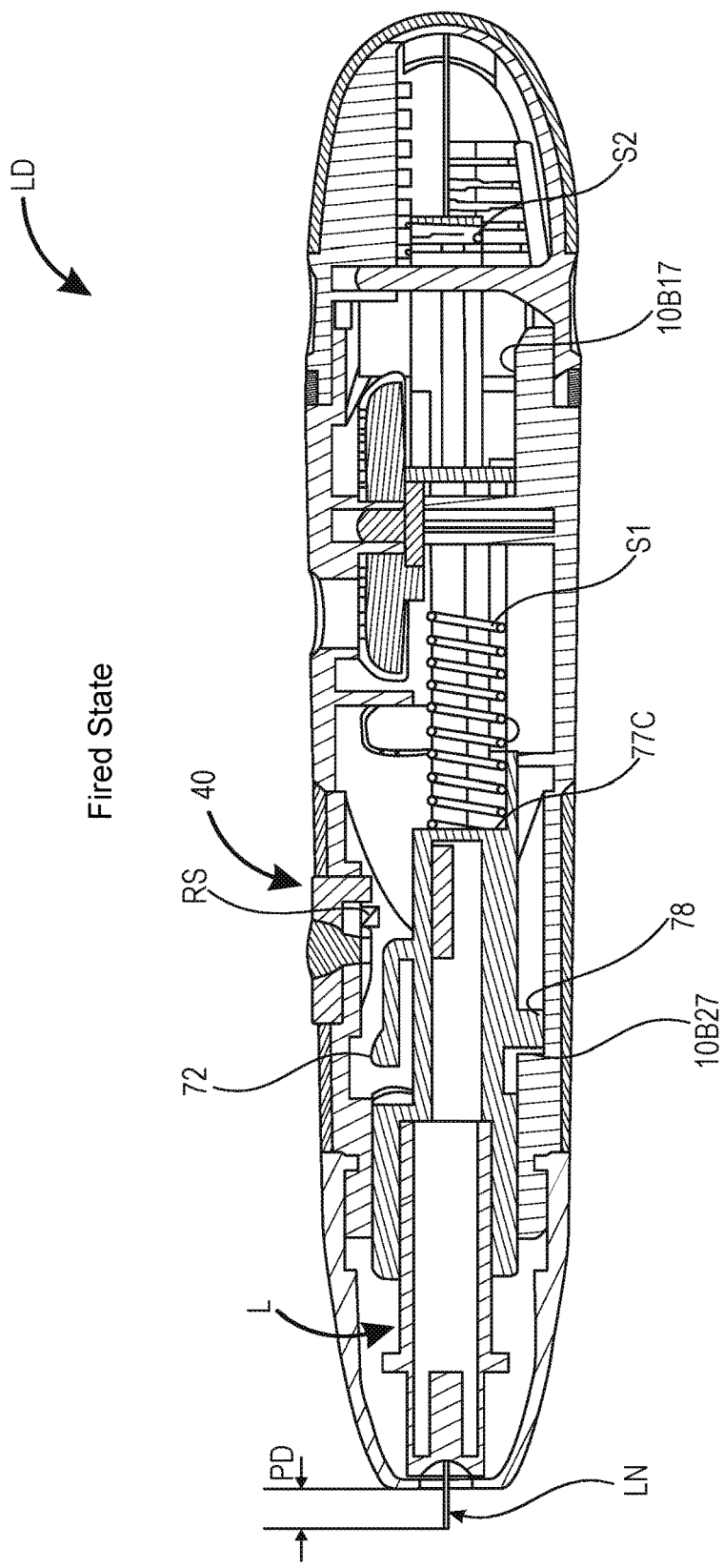
FIG. 4 shows a side cross-section view of FIG. 2. The device is shown in a triggered state and before the lancet holding member is automatically moved back to the position shown in FIG. 2.

As can be seen in FIGS. 2-4, the lancet device LD functions as follows: In the position shown in FIG. 2, the lancet device LD is shown in the static or initial position. This is the preferred position that the device would assume during shipping, storage, and after the device is triggered or fired. In this position, the drive spring S1 is in a relaxed or non-compressed or expanded position. The back or arming spring S2 is in a slightly compressed state so as to apply a biasing force that forces the back cap 30 to a forward-most position. The advance button 50 and the trigger 40 are also in an initial position. The slide spring S3 (not visible in FIG. 2) is in a slightly compressed state so as to apply a biasing force that forces the ejection slide member 50 to a rearward-most position.

In the position shown in FIG. 3, the lancet device LD is shown in the loading, armed or trigger-set position. This is the position which arms the lancet device and occurs when the user moves the back cap 30 rearward to cause the deflecting member 72 to become releasably locked to the retaining shoulder RS. In this position, the spring S1 is in a compressed state or position. Spring S2 is in an almost relaxed or a more expanded state or position, but is still able to bias the back cap 30 toward an initial position. The arming or armed position shown in FIG. 3 can take place when the user grips the back cap 30 with one hand and the body 10 with the other hand and pulls the back cap 30 away from the body 10, and then lets go of the back cap 30.

In the position shown in FIG. 4, the lancet device LD is shown in the firing or fired position. This is the position in which a user depresses the trigger 40 so as to cause the member 72 to deflect inwardly and release from the shoulder RS. This releases the energy stored in the spring S1 and causes the lancet holding member 70 to move forwardly, which automatically causes the lancet L to project out of the front surface of the front cap 20 and cause a puncture in a user's skin. Of course, the position shown in FIG. 4 merely shows a snap-shot of the lancet needle LN in the extended or puncturing position, i.e., defined by the puncturing depth PD. In actuality, the lancet needle LN would move from the position in FIG. 3 (fully retracted or trigger-set position) to that of FIG. 4 (fully extended or puncturing position), and then finally to that of FIG. 2 (initial position) in a fraction of a second. In the firing position, the spring S1 is in a substantially fully expanded position owing to the forward movement of the member 70 as caused by the rapid axial expansion of the spring S1 acting on the flange of surface 77c of member 70. After the member 70 moves to a maximum forward position shown in FIG. 4, as determined by contact between a free end of the lancet L and an inner surface of the front cap 20 and/or by contact between the projection 78 and projection 10B27, the spring S2, which has substantially reached a maximum amount of allowable compression, will expand axially back to an original position, which, in turn, places the lancet device LD back in the position shown in FIG. 2. At this point, the user has the option of activating the lancet advancing system LES (see FIGS. 7-9) in order to cause removal of the front cap 20 and to allow for removal of the used lancet L so that the next or a fresh lancet can be placed on the lancet holding member 70.

Figure 5:
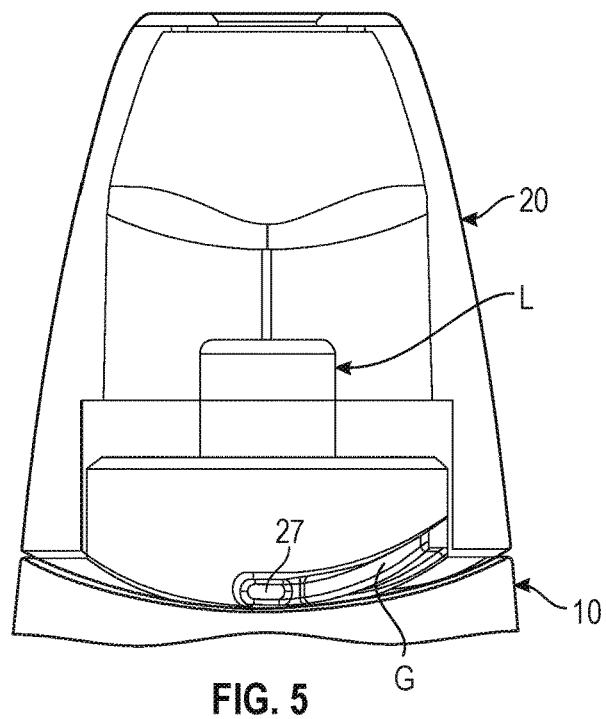
FIGS. 5 and 6 show an enlarged partial views of a front portion of the lancet device shown in FIG. 1 with the front cap being represented as transparent.
Figure 6:
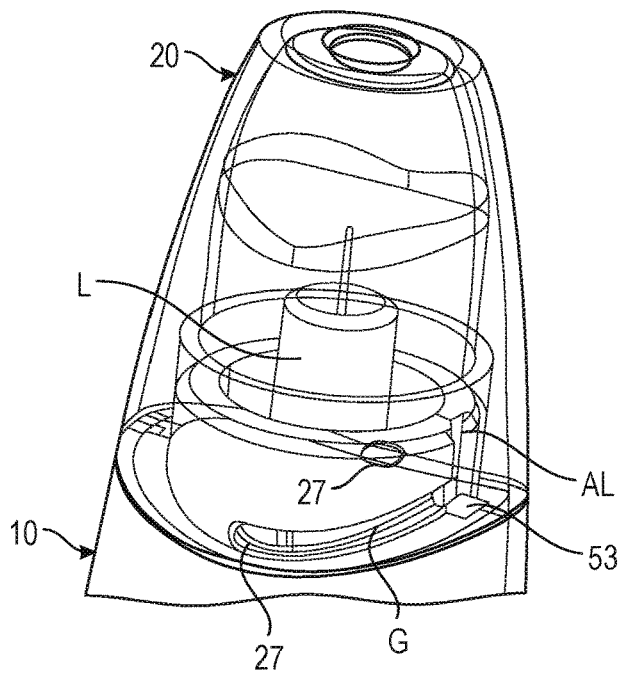

With reference to FIGS. 5 and 6, it can be seen that the lancet device LD includes a removable front cap 20 which covers a front area of the lancet device LD that includes a front end of the lancet holding member 70 and a lancet L. The lancet L is axially retained inside an elongated cylindrical opening LRO (see FIG. 44) of the lancet holding member 70 by deflectable portions of the front end portion 71a which engages with an outer cylindrical surface of the lancet L. Thus, when the lancet holding member 70 moves axially within housing 10, the lancet L moves along therewith. As is apparent from FIGS. 5 and 6, the front cap 20 can be removably secured to the housing 10 via engagement between oppositely arranged projections 27 and grooves G formed in housing parts 10A and 10B. Other types of connections can be utilized such as a snap connection of the type disclosed in U.S. Pat. No. 5,908,434 to SCHRAGA and U.S. Pat. No. 6,530,937 to SCHRAGA. The disclosure of each of these documents is hereby expressly incorporated by reference in its entirety. In order to remove the front cap 20, the user can either rotate the front cap 20 relative to the housing 10 (by e.g., about 90 degrees) to cause the projections 27 to align with oppositely arranged axial slots AL and then simply pull the front cap 20 away from the housing 10 or the user can move the slide member 50 forward (see FIGS. 7 and 9) to cause the end 53 to move into engagement with end 21 of the front cap 20 and thereby cause the projections 27 to come out of snap engagement with the grooves G.

Figure 7:
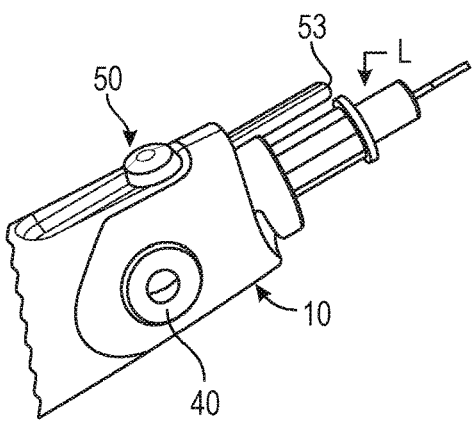
FIG. 7 shows a partial view of a front portion of the device of FIG. 1 with the front cap removed and after the lancet ejection system has been moved to a lancet ejection position.
Figure 8:
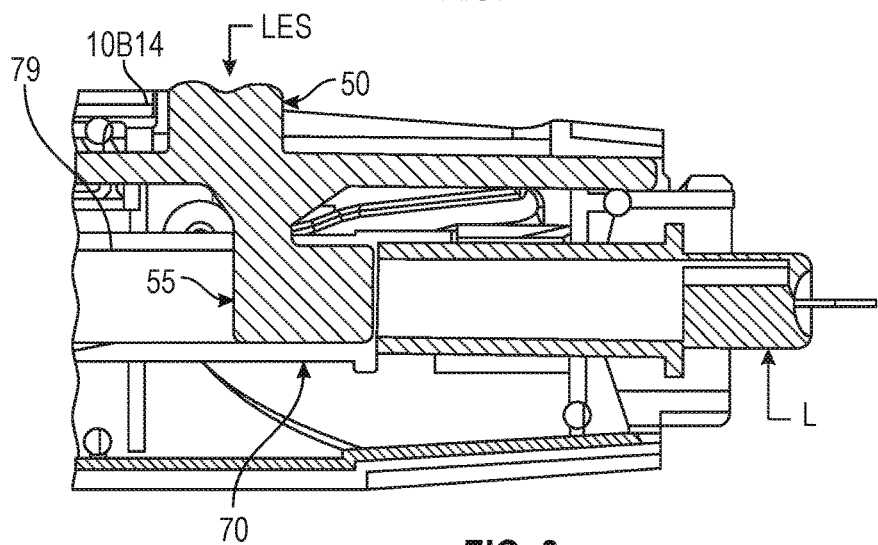
FIG. 8 shows a cross-section view of the front portion shown in FIG. 7 after the lancet ejection system has been allowed to move to an initial position.
Figure 9:
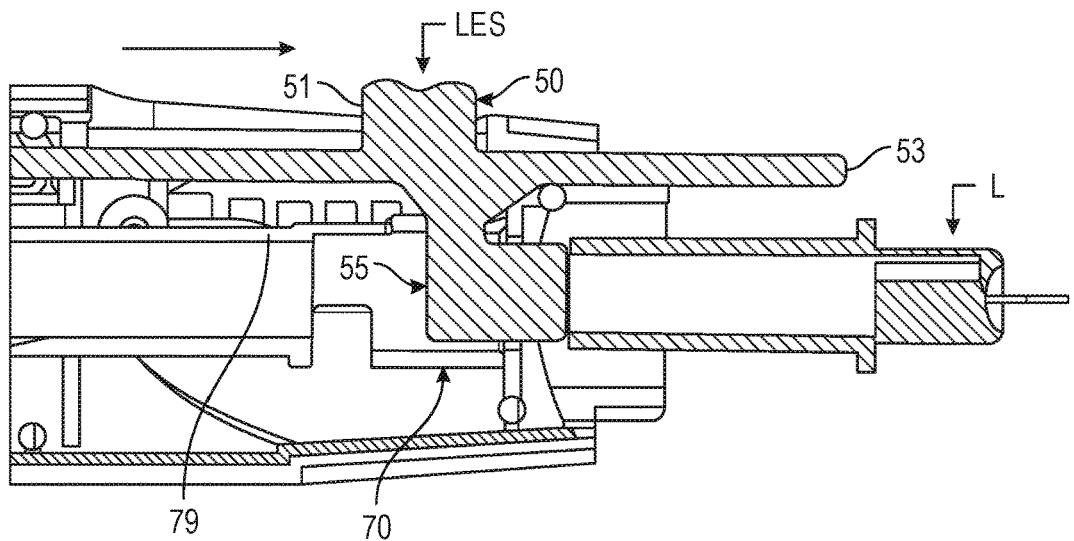
FIG. 9 shows a cross-section view of the front portion shown in FIG. 7.
Figure 12:
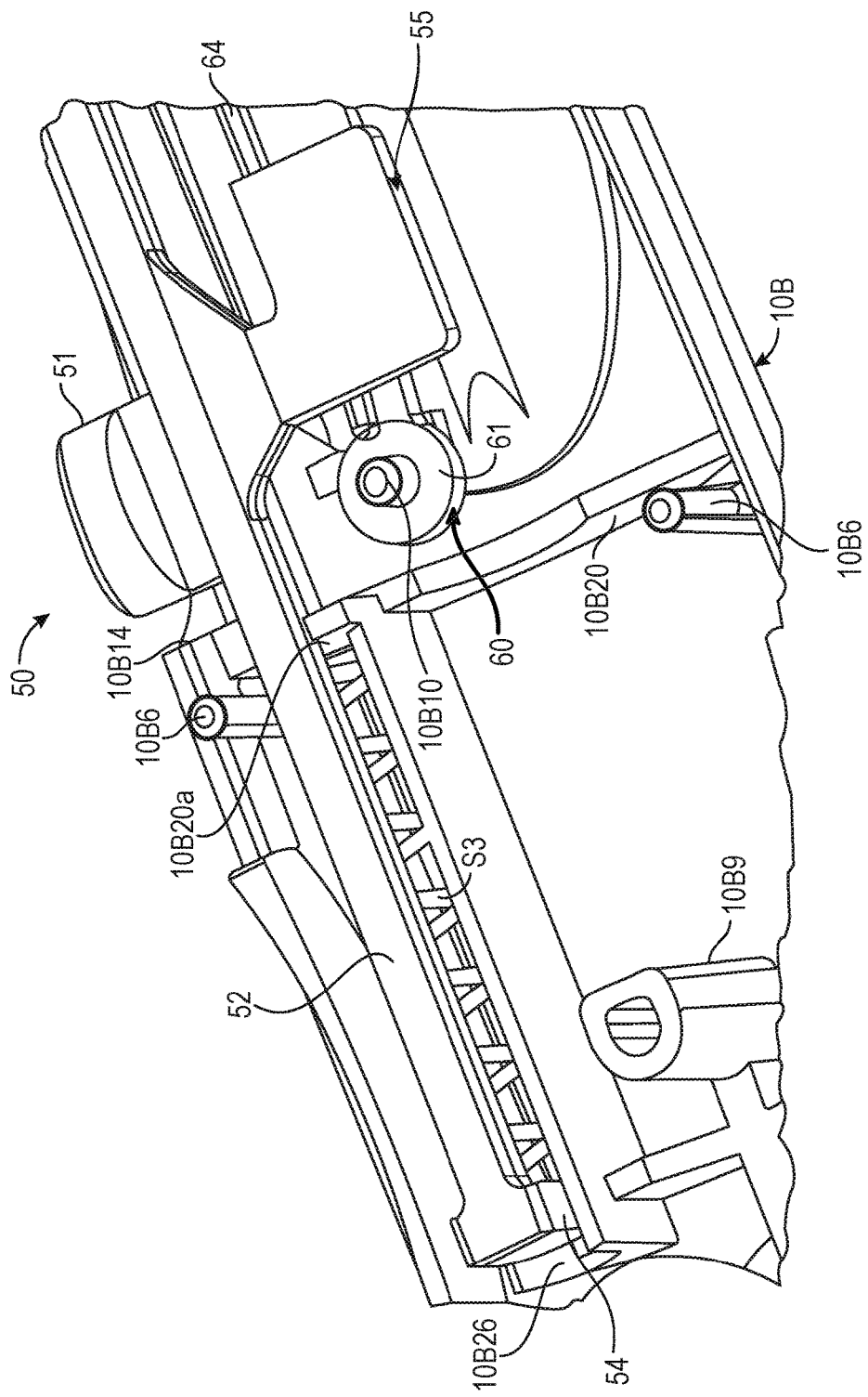
FIG. 12 shows a top partial view of a middle portion (top housing part and lancet holding member removed) of the device of FIG. 1 with the lancet ejection system in an initial position.

The details of the lancet ejecting system LES will now be described with reference to FIGS. 7-12. FIG. 8 shows the system LES in an initial position. In this position, the slide member 50 has a button portion 51 abutting or substantially near surfaces 10A14 and 10B14 (see FIGS. 22 and 24). FIGS. 7 and 9 show the system LES in a final or activated position. In this position, the slide member 50 has a button portion 51 abutting or substantially near surfaces 10A15 and 10B15 (see FIGS. 22 and 24). A spring S3 is arranged in a retaining groove 10B26 and applies a biasing force against surface 10B20a and a surface of member 54 (see FIG. 12). In operation, the advance button 50 is slid forward from the position shown in FIG. 8 to the position shown in FIGS. 7 and 9. This causes compression of the spring S3 and causes the lancet engaging member 55 (which extends into the holding member 70 via the elongated slot 79) to engage or contact a rear end of lancet L. However, when the slide member 50 is slid forward slightly against the biasing force of spring S3, this initial forward movement of the slide member 50 automatically causes the locking member 60 to pivot about axle projection 10B10 so that projection 65 engages with shoulder 78 (see FIG. 10) of the lancet holding member 70. This pivoting movement of the locking member 60 occurs as a result of sliding interaction between the guide projection 64 and the guide groove 57. Continued forward sliding movement of the slide member 50 causes the lancet L to move or advance forwards (until finally ejected) while the lancet holding member 70 is axially retained by the locking member 60. This forward movement of the slide member 50 maintains the locking member 60 in the locking position because of continued engagement between the guide projection 64 and the guide slot 57. Although not shown in FIGS. 7-12, the end 53 also moves with button 51 and would cause the front cap 20 to be removed along with the lancet L. This causes the front cap 20 to be ejected and allows the user to install a fresh or new lancet L. The user can then release the advance button 50 (which will be automatically retracted by the spring S3) and re-install the front cap 20 in order to place the device LD back into an initial or intermediate position shown in FIG. 2.

Figure 14:
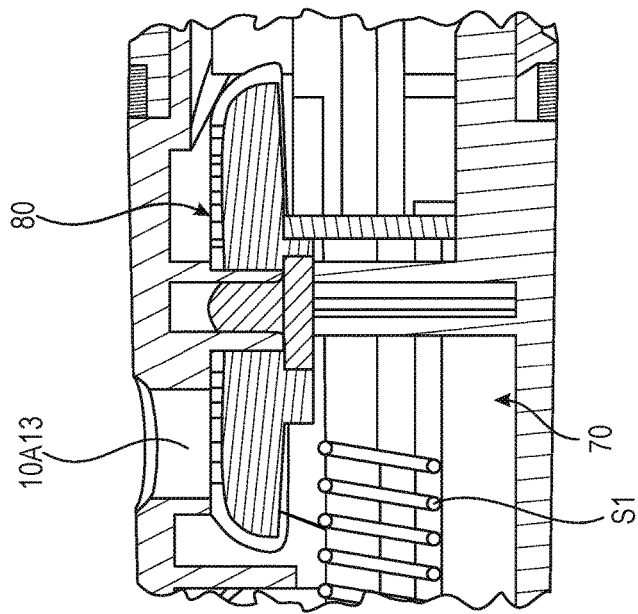
FIG. 14 shows an enlarged side cross-section view of a middle portion of the lancet device of FIG. 4 and illustrates the depth adjustment system.
Figure 15:
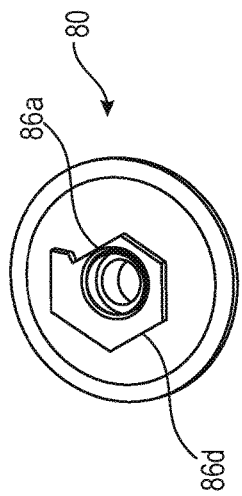
FIG. 15 shows a bottom side perspective view of the thumbwheel used in the lancet device of FIGS. 13 and 14.
Figure 13:
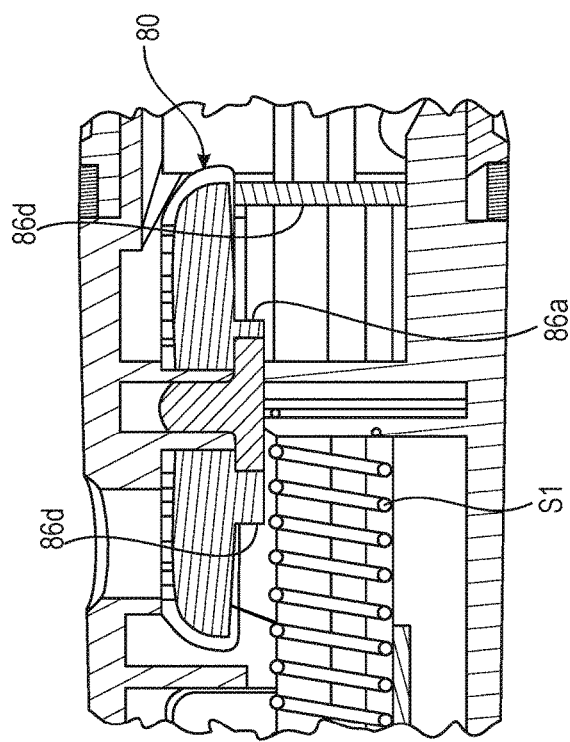
FIG. 13 shows an enlarged side cross-section view of a middle portion of the lancet device of FIG. 2 and illustrates the depth adjustment system.

With reference to FIGS. 13-15 it can be seen that the user can set a depth of penetration of the lancet device LD before the device is triggered and/or after the device is triggered. This can occur by the user rotating the thumb wheel 80 in either clockwise or counterclockwise directions. Such rotational movement determines the maximum forward position of the lancet holding member 70 and specifically projection 74. This position of the projection 74 (which contacts one of the stop surfaces 86a-86f) also determines the amount of forward axial movement of the lancet holding member 70 as discussed above. This movement changes as a result of the rotational position of the surfaces 86a-86f of the thumb wheel 80 relative to the projection 74, such that when stop surface 86a of the thumb wheel 80 is contacted by projection 74, the holding member 70 moves axially forward by a greater amount (producing a deeper puncture) than when stop surface 86f of the thumb wheel 80 is contacted by projection 74 producing a shallower puncture). The user can distinguish which stop surface 86a-86f is located in a position to be contacted by projection 74 by viewing the corresponding indicia 88 (see FIGS. 34-36) through the window or opening 10A13 in the housing 10 (see FIG. 14).

Figure 17:
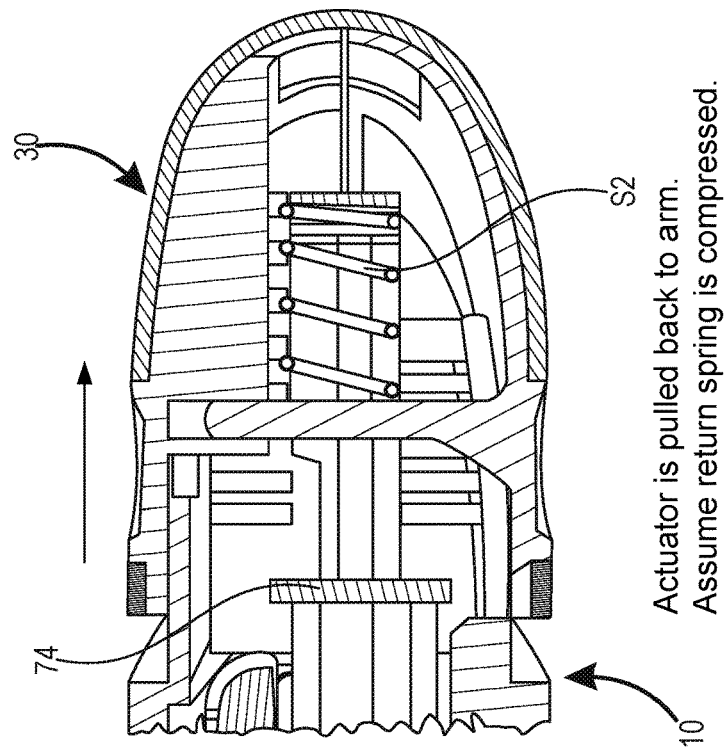
FIG. 17 shows the enlarged cross-section view of FIG. 16 and illustrates how the user can move the back cap to a trigger-set position so as to place the lancet device in the armed position of FIGS. 3 and 16.
Figure 16:
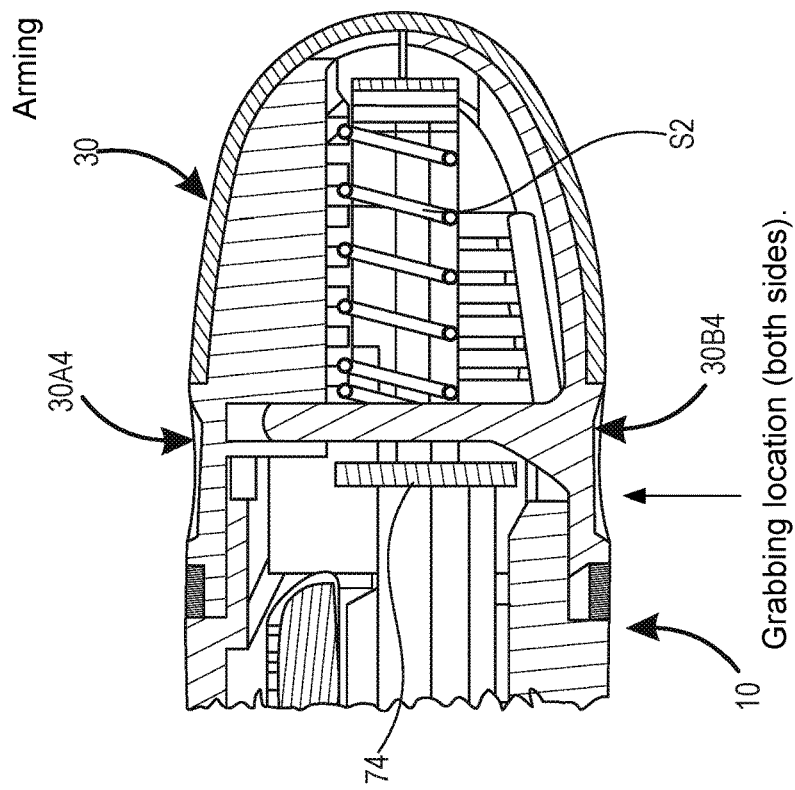
FIG. 16 shows an enlarged cross-section view of a rear portion of the lancet device of FIG. 3 and illustrates how the user can grip the back cap.

FIGS. 16 and 17 show how the lancet device LD can be armed or placed in the trigger-set position of FIG. 3. This is the position which arms the lancet device and occurs when the user moves the back cap 30 rearward to cause the deflecting member 72 to become releasably locked to the retaining shoulder RS (see FIG. 3). During this movement, the spring S2 is compressed. However, when the user releases his or her grip from the back cap 30, the spring S2 automatically causes the back cap 30 to move toward an initial position shown in FIG. 16. The user can grip the indentations 30A4 and 30B4 of the back cap 30 with one hand and the body 10 with the other hand and pull the back cap 30 away from the body 10, and then let go of the back cap 30.

Figure 19:
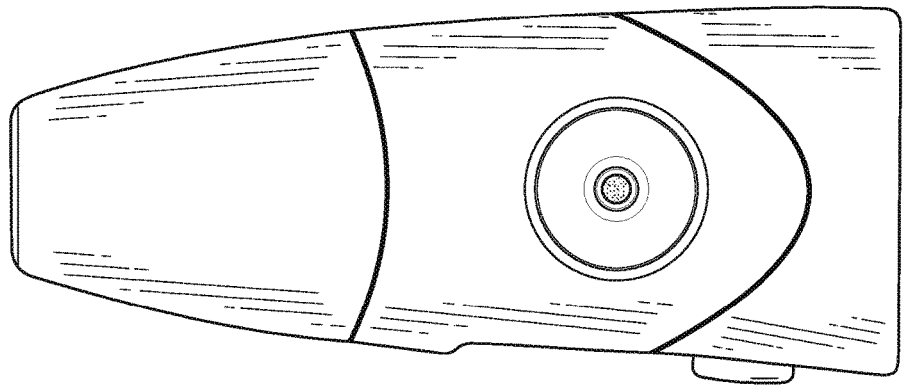
FIGS. 18 and 19 show a front portion of the lancet device of FIG. 1 and shows how a user can see a visible indicator of when the lancet device is in an armed position.
Figure 18:
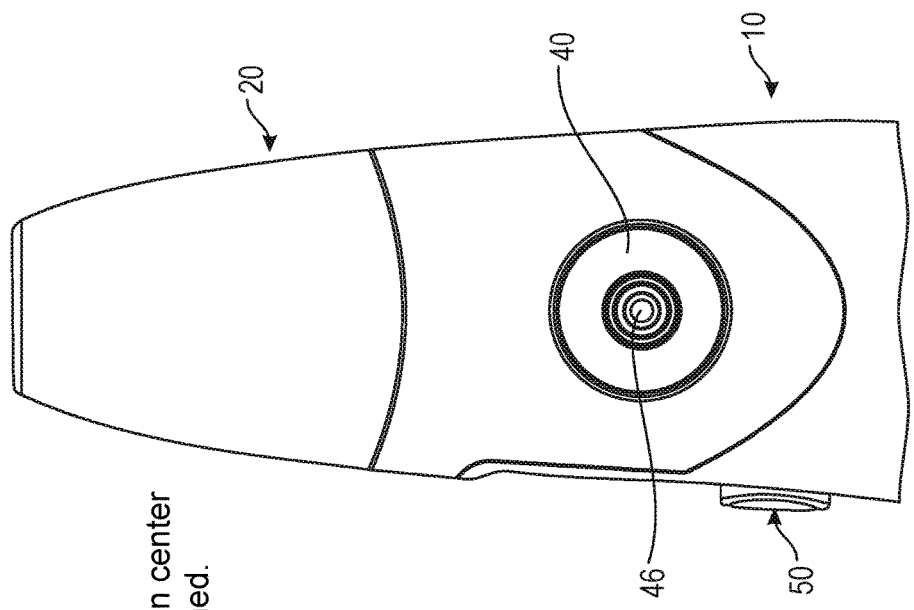

FIGS. 18 and 19 show how the lancet device LD can provide a indication to the user that the device is armed or placed in the trigger-set position of FIG. 3, thereby providing a safety feature. By way of non-limiting example, the trigger 40 includes an opening or transparent window 46 (see FIG. 38) which allows a user to see inside the device. As such, when the lancet holding member 70 is positioned in the position shown in FIG. 3, the indicator 73 (in the form of, e.g., a red dot) can be visible through the window 46 (see FIG. 43), thereby providing a visual indicator to the user of the armed position. Of course, when the lancet holding member 70 is in the position shown in FIG. 2, the indicator 73 (in the form of, e.g., a red dot) is not visible through the window 46, thereby providing a visual indicator to the user of the unarmed position.

The details of the parts utilized in the lancet device LD shown in FIGS. 1-4 will now be described with reference to FIGS. 20-49.

Figure 20:
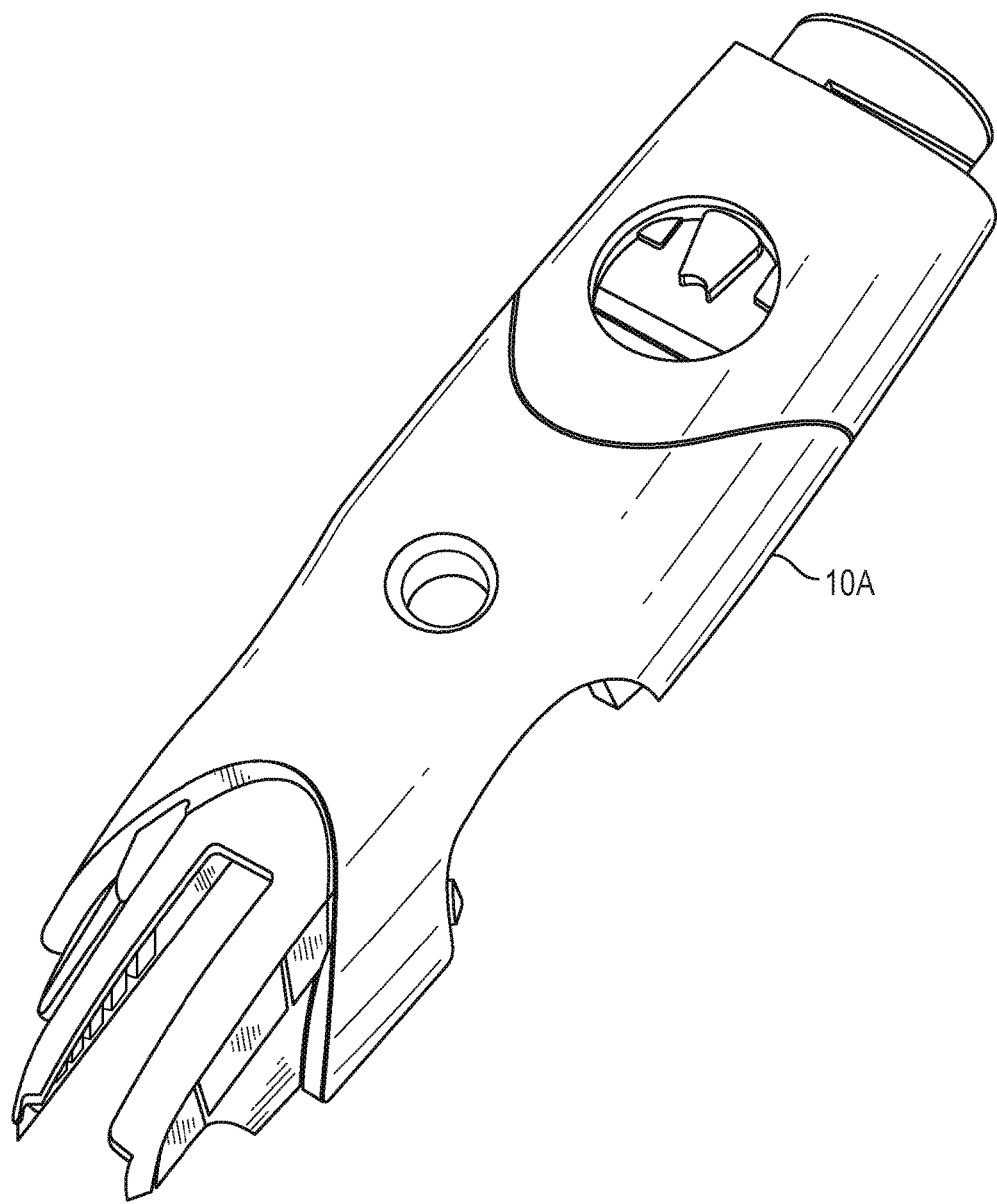
FIG. 20 shows a perspective top side view of the upper or right-side housing part used in the two-piece housing of the lancet device shown in FIG. 1.
Figure 22:
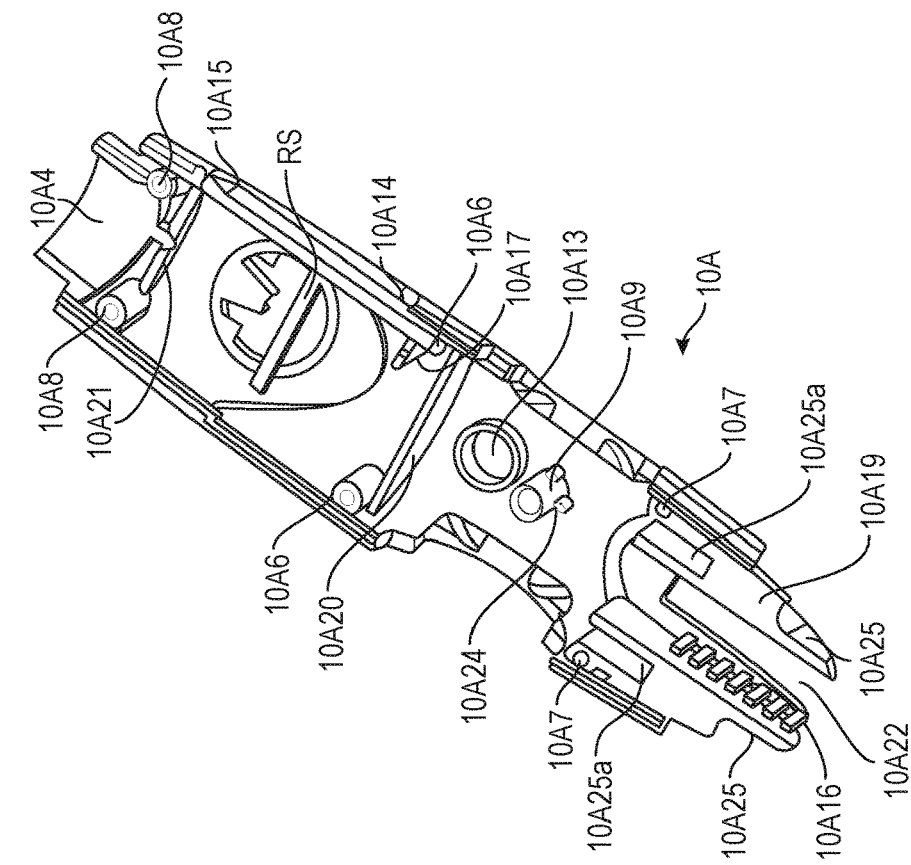
FIG. 22 shows a perspective inside view of the upper housing part shown in FIG. 21.
Figure 21:
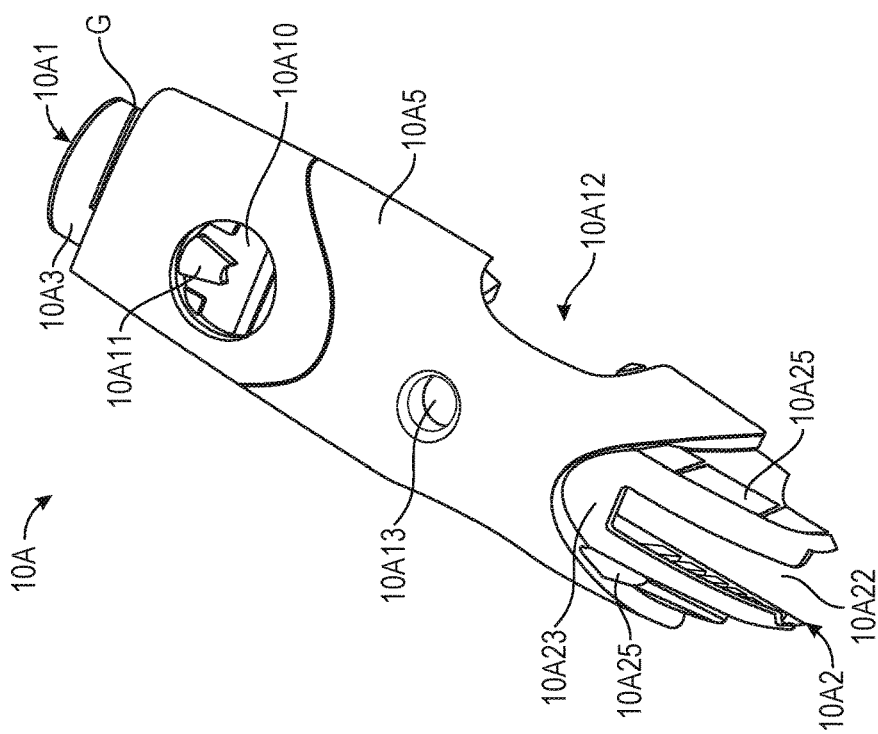
FIG. 21 shows a perspective outside view of the upper housing part shown in FIG. 20.

With reference to FIGS. 20-22, it can be seen that the upper housing part 10A includes a front end 10A1 having a partially cylindrical inner surface 10A4 and a partially cylindrical outer surface 10A3 which serves as a mounting area for the front cap 20 as well as a rear end 10A2. A generally helical groove G is arranged on the surface 10A3 of the housing part 10A and is configured to receive therein one of the projections 27 of the front cap 20. The semi-cylindrical portion 10A3 which (together with semi-cylindrical portion 10B3) is sized and configured to slidably and rotatably receive thereon the rear end of the front cap 20. The housing part 10A also has a main body portion 10A5 which is preferably ergonomically shaped. Oppositely arranged integrally formed projections 10A6 each extend or projects inwardly from the body portion 10A5 and includes a mounting opening which is sized and configured to receive therein one of the mounting projections 10B6. Oppositely arranged integrally formed projections 10A7 each extend or projects inwardly from the body portion 10A5 and includes a mounting opening which is sized and configured to receive therein one of the mounting projections 10B7. Oppositely arranged integrally formed projections 10A8 each extend or projects inwardly from the body portion 10A5 and includes a mounting opening which is sized and configured to receive therein one of the mounting projections 10B8. A centrally arranged mounting projection 10A9 extends inwardly from the body portion 10A5 and is sized to allow the thumbwheel 80 to be rotatably mounted thereto. Projections 10A24 are configured to function as a bearing surface for the surface 81 of the thumbwheel 80. A trigger opening 10A10 is formed in the body portion 10A5 and is sized and configured to receive therein the projecting portions 43a and 43b of the trigger 40 (see FIGS. 37-39). Once inserted in the opening 10A10, the projecting portions 43a and 43b of the trigger 40 prevent removal of the trigger 40 from the housing part 10A, but allow the trigger 40 to move against the biasing force of an integrally formed deflecting member 10A11 which functions as a flat spring and bias the trigger 40 towards an extended or initial position. The deflectable member 10A11 is deflected by contact with projection 44 of the trigger 40 when the trigger 40 is depressed. A retaining shoulder RS is formed in the body portion 10A5 and is configured to releasably engage and/or lock with a deflecting portion 72 of the lancet holding member 70 (see FIGS. 42-44). Oppositely arranged indented sections 10A12 are arranged in an area of the middle rear end of the housing part 10A and together with indented section 10B12 form an area for the user to activate the thumbwheel 80. A viewing opening 10A13 is arranged in the body portion 10A5 of the front end of the housing part 10A, which allows a user to view indicia 88 of the thumbwheel 80 when the thumbwheel 80 is mounted to the projection 10A9. A half-slot or half-groove defined by surfaces 10A14 and 10A15 (together with half-groove formed by surfaces 10B14 and 10B15) forms a guide groove which guides the sliding movement of the slide member 50 between an initial and final position (see FIGS. 8 and 9). The slide member 50 contacts and/or substantially abuts stop surface 10A14 in the initial position shown in FIG. 8 (as a result of the biasing force of the spring S3) and contacts and/or substantially abuts stop surface 10A15 in the final position shown in FIG. 9 (as a result of the user causing compression of the spring S3). Oppositely arranged reinforcing ribs 10A16 are also utilized. A projection 10A17 is utilized to abut projection 10B14 and prevent axial movement of the ring portion 61 of the locking member 60. A rear portion of the housing part 10A includes surface 10A19 which is configured to abut with surface 10B19 of the housing part 10B, and a groove 10A22 which slidably receives therein projection 30A6. Housing part 10A also includes reinforcing projections 10A20 and 10A21. The rear portion of the housing part 10A also includes surface 10A23 which is configured to be slidably engaged by the inner surface of portion 30A1 as well as oppositely arranged guide surfaces 10A25 which are sized and configured to be slidably engaged by the inner surfaces of members 30A3. The guide surfaces 10A25 extend into openings in the member 10A so as to form slots 10A25a (see FIG. 22). As is apparent from FIGS. 20-22, the housing part 10A can preferably be a one-piece member and is most preferably a one-piece synthetic resin member. Of course, the member 10A can also be an assembly of plural components provided it functions in a manner similar to that of the member shown in FIGS. 20-22.

Figure 23:
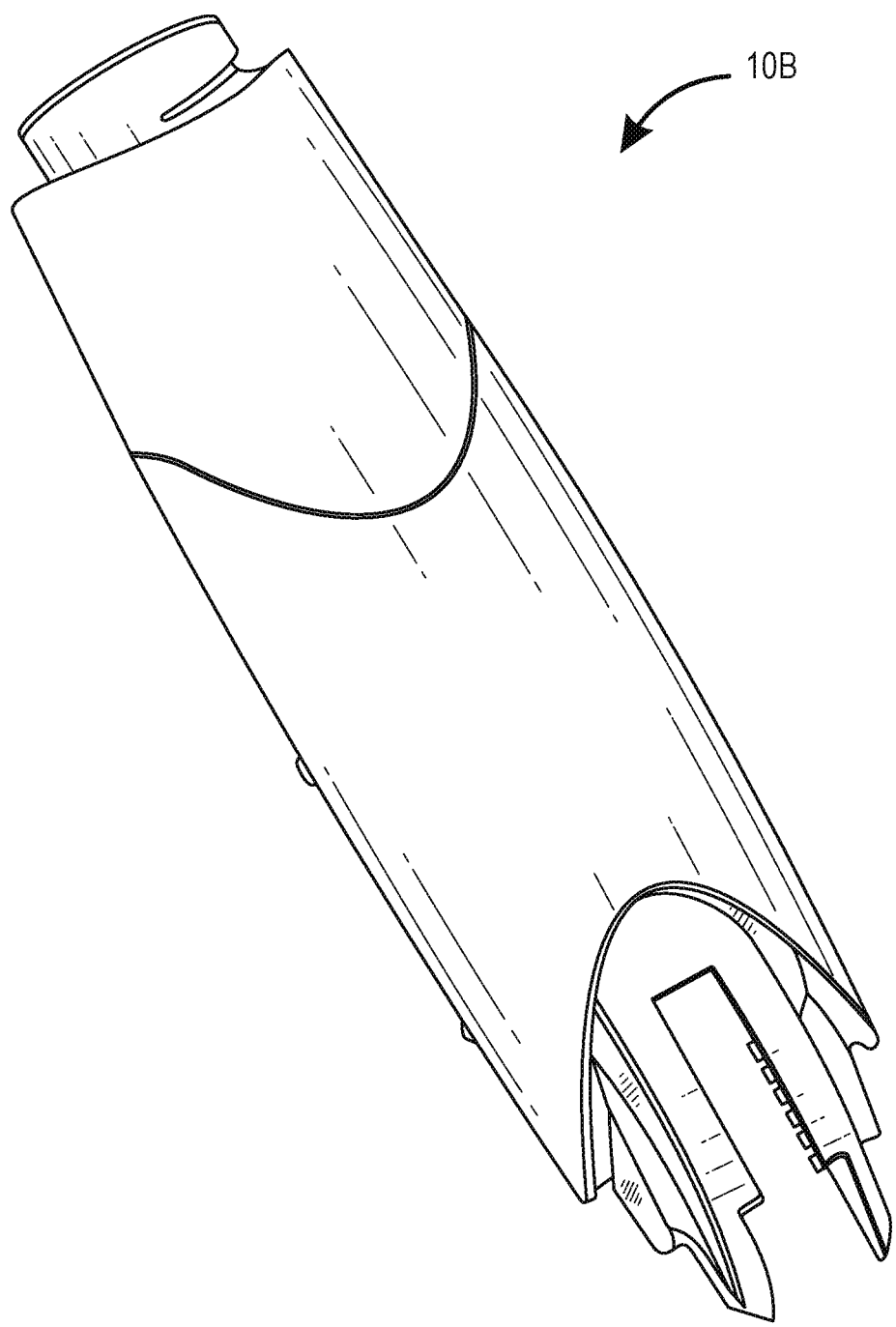
FIG. 23 shows a perspective bottom side view of the lower or left-side housing part used in the two-piece housing of the lancet device shown in FIG. 1.

With reference to FIGS. 23-25, it can be seen that the lower housing part 10B includes a front end 10B1 having a partially cylindrical inner surface 10B4 and a partially cylindrical outer surface 10B3 which serves as a mounting area for the front cap 20 as well as a rear end 10B2. A generally helical groove G is arranged on the surface 10B3 of the housing part 10B and is configured to receive therein one of the projections 27 of the front cap 20. The semi-cylindrical portion 10B3 which (together with semi-cylindrical portion 10A3) is sized and configured to slidably and rotatably receive thereon the rear end of the front cap 20. The housing part 10B also has a main body portion 10B5 which is preferably ergonomically shaped. Oppositely arranged integrally formed projections 10B6 each extend or projects inwardly from the body portion 10B5 and is sized and configured to extend into the opening of mounting projections 10A6. Oppositely arranged integrally formed projections 10B7 each extend or projects inwardly from the body portion 10B5 and is sized and configured to extend into the openings in the mounting projections 10A7. Oppositely arranged integrally formed projections 10B8 each extend or projects inwardly from the body portion 10B5 and are sized and configured to extend into the mounting openings of the mounting projections 10A8. A centrally arranged D-shaped guide projection 10B9 extends inwardly from the body portion 10B5 and has an upper surface 10B24 configured to abut surface 87 of the thumbwheel 80. The projection 10B9 also extends through the slot 77b and into the space 77a of the holding member 70, and participates in guiding the axial movement of the holding member 70. A guide surface arrangement 10B11 is formed in the body portion 10B5 and is configured to support and allow for the sliding and/or pivoting movement of the locking member 60 (see FIG. 11). Oppositely arranged indented sections 10B12 are arranged in an area of the middle rear end of the housing part 10B and together with indented section 10A12 form an area for the user to activate the thumbwheel 80. Oppositely arranged support surfaces 10B13 are arranged on the body portion 10B5 and are configured to be slidably engaged by the surface 82 of the thumbwheel 80. A half-slot or half-groove defined by surfaces 10B14 and 10B15 (together with half-groove formed by surfaces 10A14 and 10A15) forms a guide groove which guides the sliding movement of the slide member 50 between an initial and final position (see FIGS. 8 and 9). The slide member 50 contacts and/or substantially abuts stop surface 10B14 in the initial position shown in FIG. 8 (as a result of the biasing force of the spring S3) and contacts and/or substantially abuts stop surface 10B15 in the final position shown in FIG. 9 (as a result of the user causing compression of the spring S3). Oppositely arranged reinforcing ribs 10B16 are also utilized. A projection 10B17 is utilized to support and guide the movement of a middle rear portion of the holding member 70 (see FIGS. 2 and 4). A rear portion of the housing part 10B includes surface 10B19 which is configured to abut with surface 10A19 of the housing part 10A, and a groove 10B22 which slidably receives therein projection 30B6. Housing part 10B also includes reinforcing projections 10B18, 10B20 and 10B21, and each of these projections utilize a semi-circular recess which slidably supports the lancet holding member 70. The rear portion of the housing part 10B also includes surface 10B23 which is configured to be slidably engaged by the inner surface of portion 30B1 as well as oppositely arranged guide surfaces 10B25 which are sized and configured to be slidably engaged by the inner surfaces of members 30B3. The guide surfaces 10B25 extend into openings in the member 10B so as to form slots 10B25a (see FIG. 24). An elongated recess or groove 10B26 is formed in the member 10B5 and is sized to receive therein the spring S3 and be slidably engaged by the projection 54 (see FIG. 12). A projection 10B27 is utilized to support and guide the movement of a front portion of the holding member 70. As is apparent from FIGS. 23-25, the housing part 10B can preferably be a one-piece member and is most preferably a one-piece synthetic resin member. Of course, the member 10B can also be an assembly of plural components provided it functions in a manner similar to that of the member shown in FIGS. 23-25.

Figure 26:
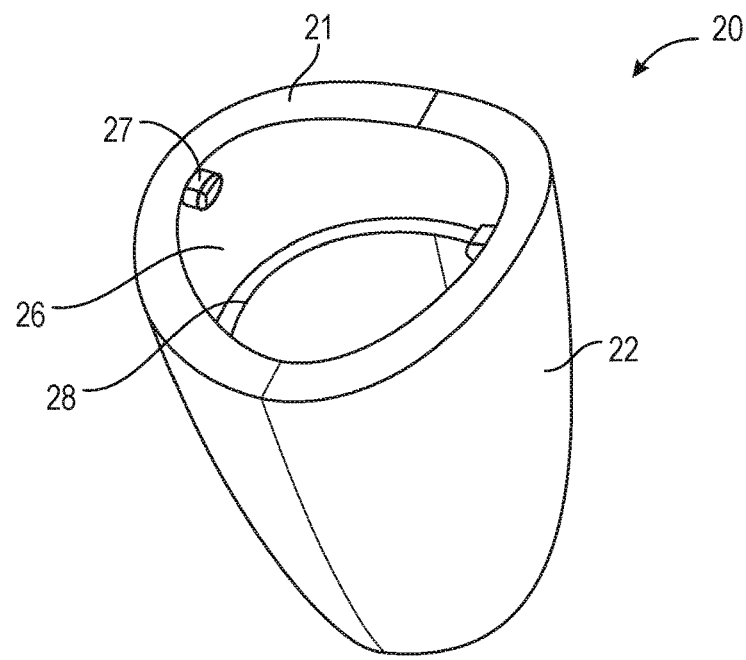
FIG. 26 shows a perspective inside view of the front cap used in the lancet device shown in FIG. 1.
Figure 27:
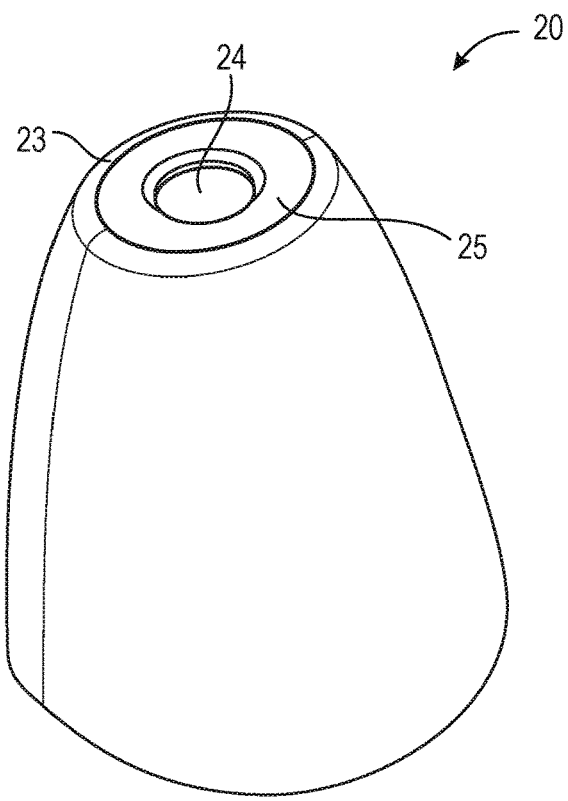
FIG. 27 shows a perspective outside view of the front cap shown in FIG. 26.

With reference to FIGS. 26 and 27, it can be seen that the front cap 20 includes a skin contacting surface 25 which includes a lancet needle opening 24 sized and located to allow one of the lancet needles LN to pass or extend there through. The front cap 20 has an outer tapered generally circular surface 22, a rear end 21, and a generally planar front surface 23 The front cap 20 preferably include mechanisms, i.e., oppositely arranged projections 27, arranged on inner generally cylindrical surface 26 to ensure that the front cap 20 is removably mounted to the grooves G of the front end of the housing 10. A shoulder 28 is structured and arranged to be contacted by the end 53 of the slide member 50 (so as to allow the slide member 50 to pop-off the front cap 20), and to abut the ends 10A1 and 10B1 of the housing parts 10A and 10B. As is apparent from FIGS. 26 and 27, the front cap 20 can preferably be a one-piece member and is most preferably a one-piece synthetic resin member. Of course, the front cap 20 can also be an assembly of plural components provided it functions in a manner similar to that of the member shown in FIGS. 29 and 30.

With reference to FIGS. 28-33, it can be seen that the back cap 30 includes two main parts, i.e., upper back cap portion 30A and lower back cap portion 30B. The upper portion 30A includes a front end 30A1, a gripping indentation 30A4, a tapered and rounded portion 30A7, a rear end 30A2. The two projections 30A3 serve to guide the linear movement of the back cap 30 relative to the housing 10 by slidably engaging with the surfaces 10A25. A centrally arranged projection 30A6 extends into the groove 10A22 and has an opening which receives therein the projection 30B8 of the back cap part 30B. A bottom surface 30A5 is configured to abut the surface 30B5 of the part 30B and has openings which receive therein the projection 30B9 of the back cap part 30B. The lower portion 30B includes a front end 30B1, a gripping indentation 30B4, a tapered and rounded portion 30B7, a rear end 30B2. The two projections 30B3 serve to guide the linear movement of the back cap 30 relative to the housing 10 by slidably engaging with the surfaces 10B25. A centrally arranged projection 30B6 extends into the groove 10B22 and has a projection which extend into an opening in the projection 30A6 of the back cap part 30A. A bottom surface 30B5 is configured to abut the surface 30A5 of the part 30A and has projections which extend into the openings in surface 30A5. The rear facing surface of the projection 30B6 is configured to be contacted by a front end of the spring S2. This allows the spring S2 to bias the back cap 30 towards the position shown in FIG. 16 and automatically moves the back cap 30 back to the position shown in FIG. 16 when the user releases the back cap 30 from the position shown in FIG. 17. As is apparent from FIGS. 28-33, the back cap 30 can preferably be a two-piece member and is most preferably a two-piece synthetic resin member. Of course, the back cap 30 can also be a one-piece member and/or an assembly of more than two components provided it functions in a manner similar to that of the member shown in FIGS. 28-33.

With reference to FIGS. 34-36, it can be seen that the depth adjustment member or thumb wheel 80 includes an upper bearing surface 81 which is configured to slidably engage with the projections 10A24, a rear surface 82 which is configured to slidably engage with the surfaces 10B13, and a rear surface 87 which is configured to slidably engage with the surface 10B24. In this way, the thumb wheel 80 is axially retained within the housing 10. A generally cylindrical projection 83 is sized to rotatably engaged with and mount to an opening formed in the projection 10A9. The thumb wheel 80 also includes an outer surface 84 adapted to be frictionally engaged by a user's fingers which allow a user to easily grip the thumb wheel 80 and rotate it relative to the housing 10 in each of a clockwise and counterclockwise directions. Any type of friction surface can also be utilized in the area 84. The thumb wheel 80 also includes a main projection 85. The main projection 85 includes a number or cam or stop surfaces 86a-86f which function to control the depth of penetration of the lancet needle LN and/or which control the distance PD (see FIG. 4). The depth of penetration PD is adjusted or predetermined by the rotational position of the thumb wheel 80 relative to the housing 10 and more specifically by the rotational position of the surfaces 86a-86f relative to the movably stop surface 74. Maximum depth of penetration PD results when the projection 74 contacts stop surfaces 86a whereas minimum depth of penetration PD results when the projection 74 contacts stop surface 86f. The thumb wheel 80 also utilizes indicia 88 which functions to provide the lancet device LD with a system for indicating to the user the position of depth adjustment, i.e., the rotational position of the thumb wheel 80, so that the user can determine whether to change the depth of penetration. An indicator, e.g., window 10A13, is arranged on the housing 10 and allows the user to see the indicia 88. By way of non-limiting example, the indicia value "1" (viewed in the window 10A13) can correspond to the stop surface 86f being located in a position allowing it to be contacted by the projection 74; the indicia value "2" (viewed in the window 10A13) can correspond to the stop surface 86e being located in a position allowing it to be contacted by the projection 74; the indicia value "3" (viewed in the window 10A13) can correspond to the stop surface 86d being located in a position allowing it to be contacted by the projection 74; the indicia value "4" (viewed in the window 10A13) can correspond to the stop surface 86c being located in a position allowing it to be contacted by the projection 74; the indicia value "5" (viewed in the window 10A13) can correspond to the stop surface 86b being located in a position allowing it to be contacted by the projection 74; and the indicia value "6" (viewed in the window 10A13) can correspond to the stop surface 86a being located in a position allowing it to be contacted by the projection 74. As is apparent from FIGS. 34-36, the thumb wheel 80 can preferably be a one-piece member and is most preferably a one-piece synthetic resin member. Of course, the thumb wheel 80 can also be an assembly of plural components provided it functions in a manner similar to that of the member shown in FIGS. 34-36.

With reference to FIGS. 37-39, it can be seen that the trigger 40 includes a generally circular upper surface 41 which is configured to be contacted by a user finger. The trigger 40 also includes two oppositely arranged projections 43*a* and 43*b* which are configured to snap into the opening 10A10 and prevent removal of the trigger 40 once installed on the body portion 10A. A generally circular projection 45 is configured to contact free end portion of the deflectable member 10A11. The projection 45 has a opening 47 which is aligned with a window 46 and together allows the user to view the red indicator 73 when the lancet device LD is in the trigger-set position. A generally rectangular projection 44 is configured to contact the deflectable member 72 and cause the shoulder of the deflectable member 72 (see FIG. 43) to disengage from the retaining shoulder RS after the lancet device LD is in a trigger-set position (see e.g., FIG. 3) and the trigger 40 is depressed. As is apparent from FIGS. 37-39, the trigger 40 can preferably be a one-piece member and is most preferably a one-piece synthetic resin member. Of course, the trigger 40 can also be an assembly of plural components provided it functions in a manner similar to that of the member shown in FIGS. 37-39.

Figure 41:
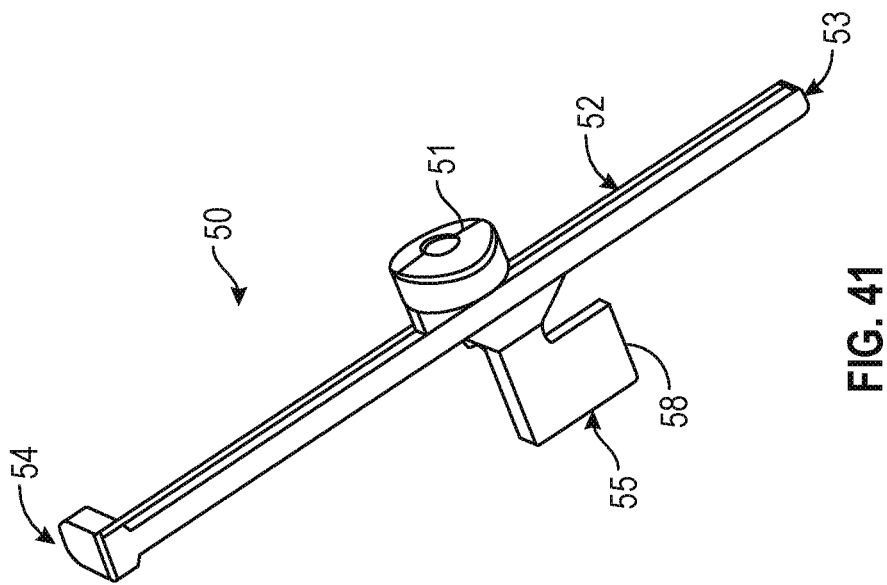
FIG. 41 shows a top side perspective view of the lancet ejection member shown in FIG. 40.
Figure 40:
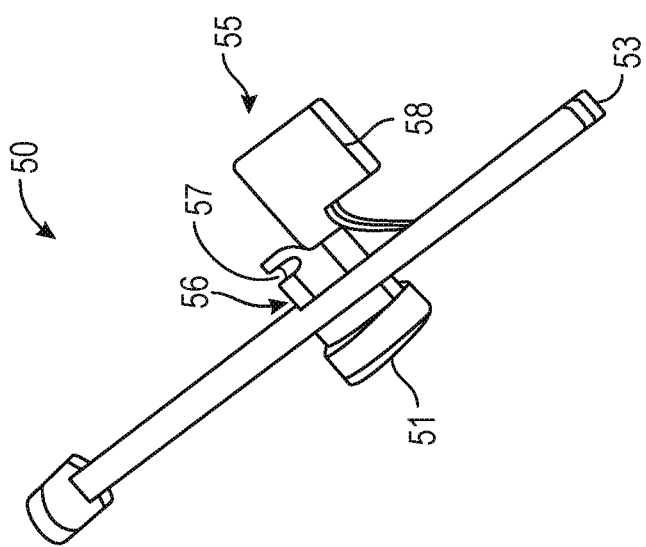
FIG. 40 shows a bottom side perspective view of the lancet ejection member used in the lancet device shown in FIG. 1.

With reference to FIGS. 40 and 41, it can be seen that the slide or advance member 50 includes a generally circular button portion 51 which is configured to be contacted by a user finger. A front free end 52 is arranged on one end of a main portion 52 and is configured to contact the shoulder 28 of the front cap 20. A rear projection 54 is arranged on another end of a main portion 52 and is configured to contact a rear end of the spring S3 (see FIG. 12). A generally rectangular projection 55 is configured to extend into and slide within the slot 79 of member 70. The member 55 has a front edge 58 that is configured to engage or contact a rear surface of the lancet L and has two oppositely arranged planar surfaces. A through slot 57 is formed on member 56 and is configured to slidably engage with cam projection 64 of locking member 60. As is apparent from FIGS. 40 and 41, the advance button 50 can preferably be a one-piece member and is most preferably a one-piece synthetic resin member. Of course, the member 50 can also be an assembly of plural components provided it functions in a manner similar to that of the member shown in FIGS. 40 and 41.

Figure 42:
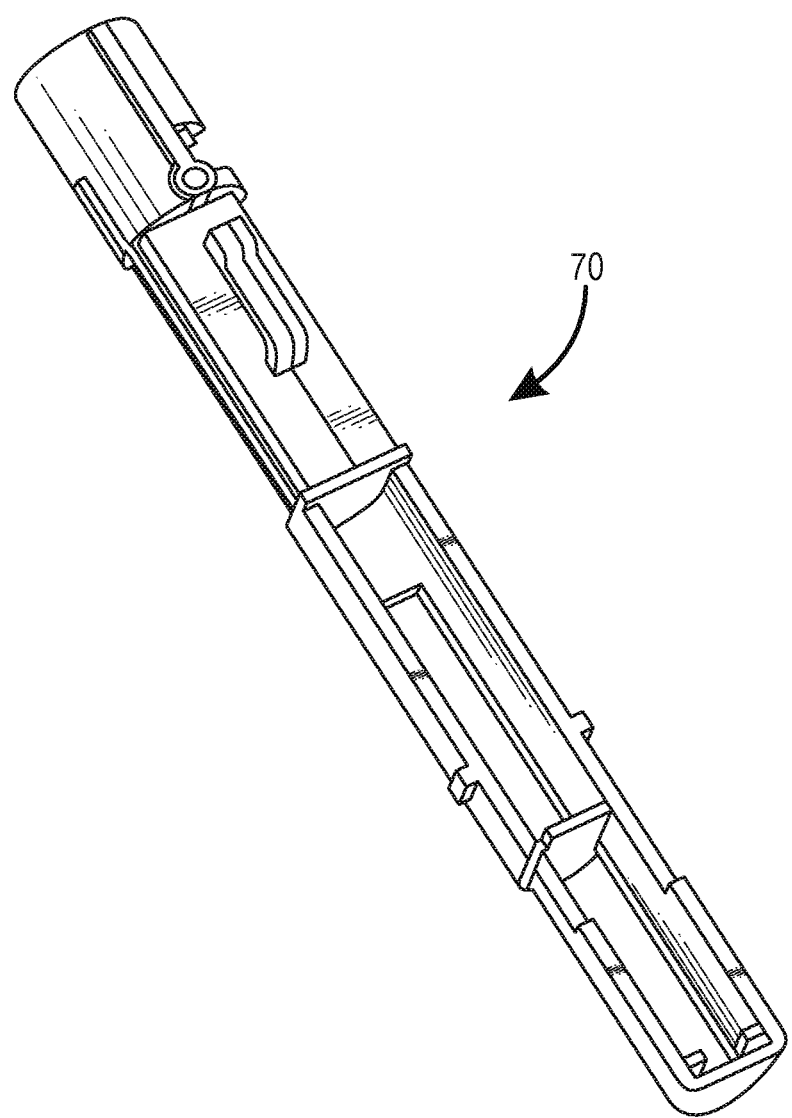
FIG. 42 shows a top perspective view of the lancet holding member used in the lancet device shown in FIG. 1.
Figure 44:
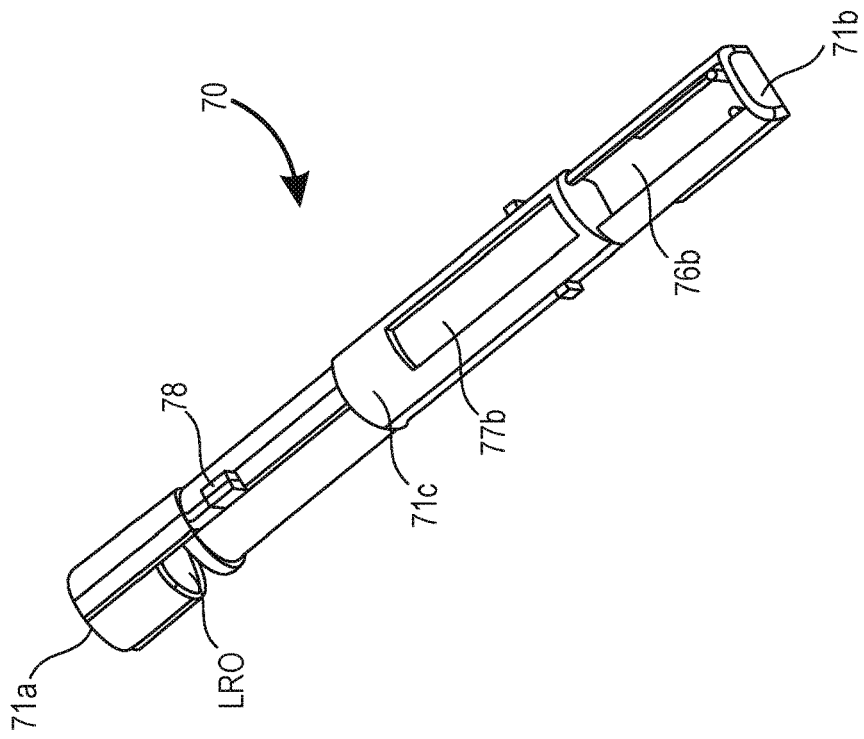
FIG. 44 shows a bottom right-side perspective rear side view of FIG. 43.
Figure 43:
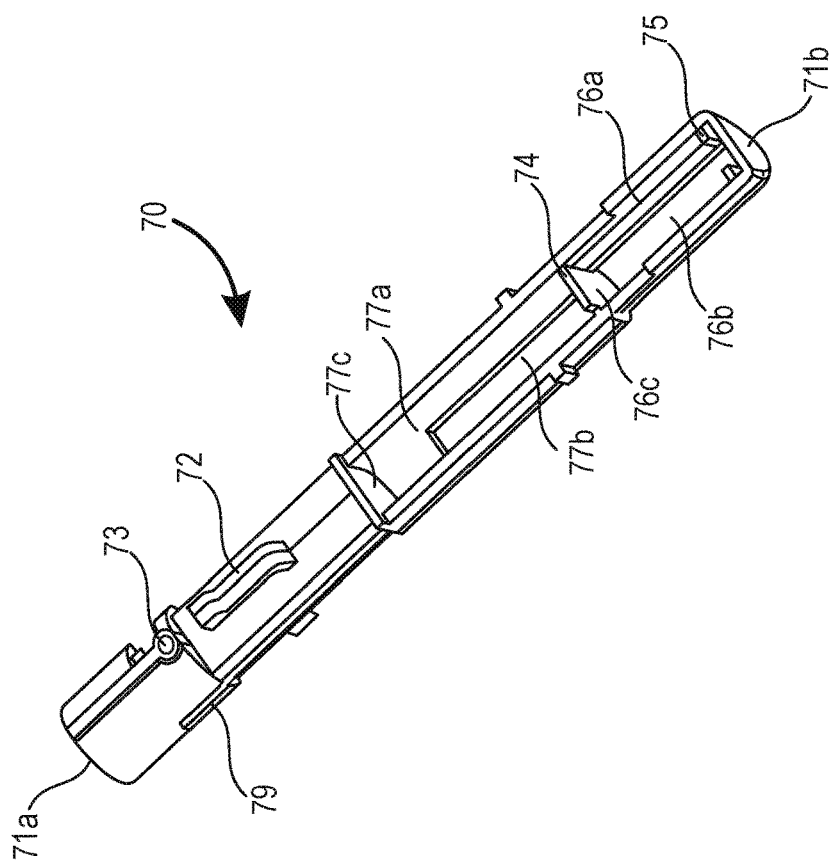
FIG. 43 shows a top left-side perspective view of FIG. 42.

With reference to FIGS. 42-44, it can be seen that the lancet holding member 70 includes an annular front end 71*a* having a generally cylindrical opening LRO sized to receive therein a lancet L, and a rear end 71*b* which includes a shoulder 75 configured to retain therein a rear end of the spring S2. The member 70 has a generally cylindrical body portion 7*c* sized to slidably engaged with support and guide surfaces of the housing parts 10A5 and 10B5. The member 70 also includes a deflectable projection 72 which is configured to releasably lock to retaining shoulder RS. A color, e.g., red, indicator dot 73 is provided to indicate to the user when the holding member 70 is located in a trigger-set position. The member 70 also includes a stop projection 74 which is configured to contact one of the plurality of stop surfaces 86*a*-86*f*. A semi-cylindrical area 77*a* is sized to receive therein the spring S1 whereas semi-cylindrical area 76*a* is sized to receive therein the spring S2. The elongated slot 77*b* is sized to receive therein 10B9 and the elongated slot 76*b* is sized to receive therein 30B6. The surface 77*c* is configured to be contacted by a front end of the spring S1.

An elongated slot 79 is sized to slidably receive therein the lancet ejecting portion 55 of the slide member 50. The member 70 also includes a stop projection 78 which is configured to contact and slidably engage guide surface 10B28, and can optionally engage with the stop projection 10B27. As is apparent from FIGS. 42-44, the member 70 can preferably be a one-piece member and is most preferably a one-piece synthetic resin member. Of course, the member 70 can also be an assembly of plural components provided it functions in a manner similar to that of the member shown in FIGS. 42-44.

Figure 47:
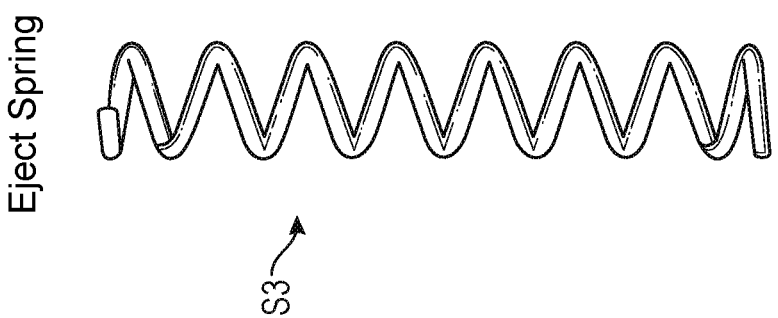
FIG. 47 shows a perspective side view of the spring used to bias the lancet ejection system of the lancet device shown in FIG. 1.
Figure 46:
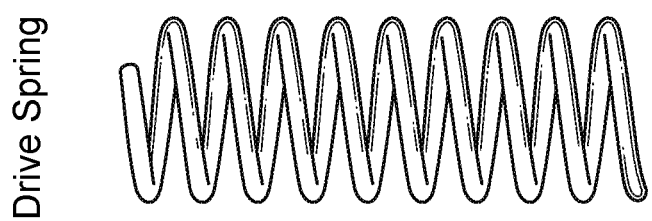
FIG. 46 shows a perspective side view of the drive spring which causes the lancet holding member to move to the puncturing position of the lancet device shown in FIG. 1.
Figure 45:
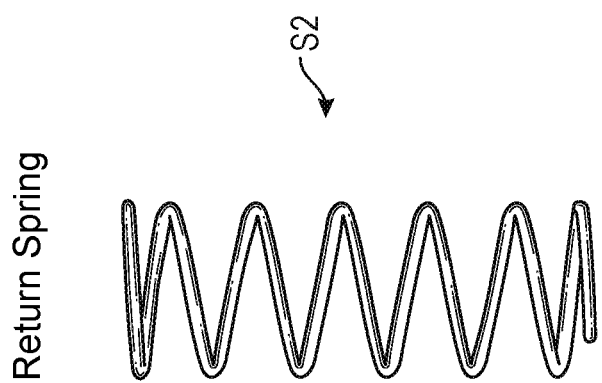
FIG. 45 shows a perspective side view of the lancet holding member/back cap return spring used on the lancet device of FIG. 1.

With reference to FIGS. 45-47, it can be seen that the main spring S1, the return spring S2 and the slide member return spring S3 can have the form of helical wire compression springs. Each spring S1-S3 is preferably be a one-piece member and is most preferably a one-piece spring metal member. Of course, the springs can also be made of any material provided they function in a manner similar to that of the members shown in FIGS. 45-47.

Figure 49:
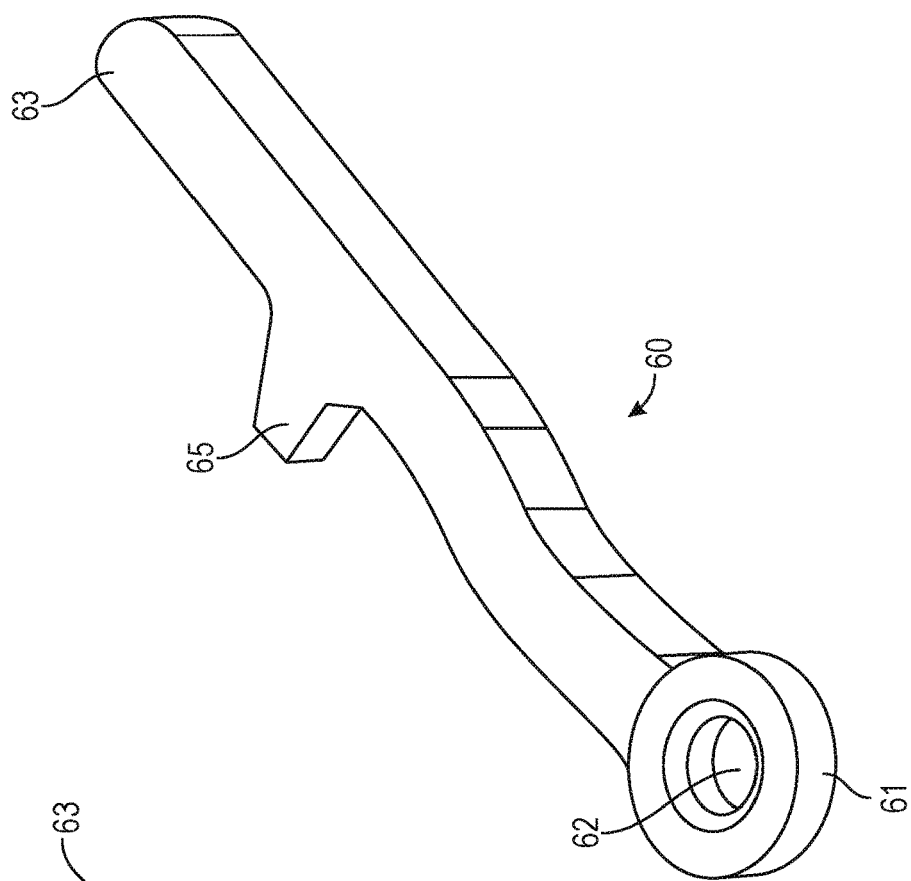
FIG. 49 shows a bottom perspective view of the locking member shown in FIG. 48.
Figure 48:
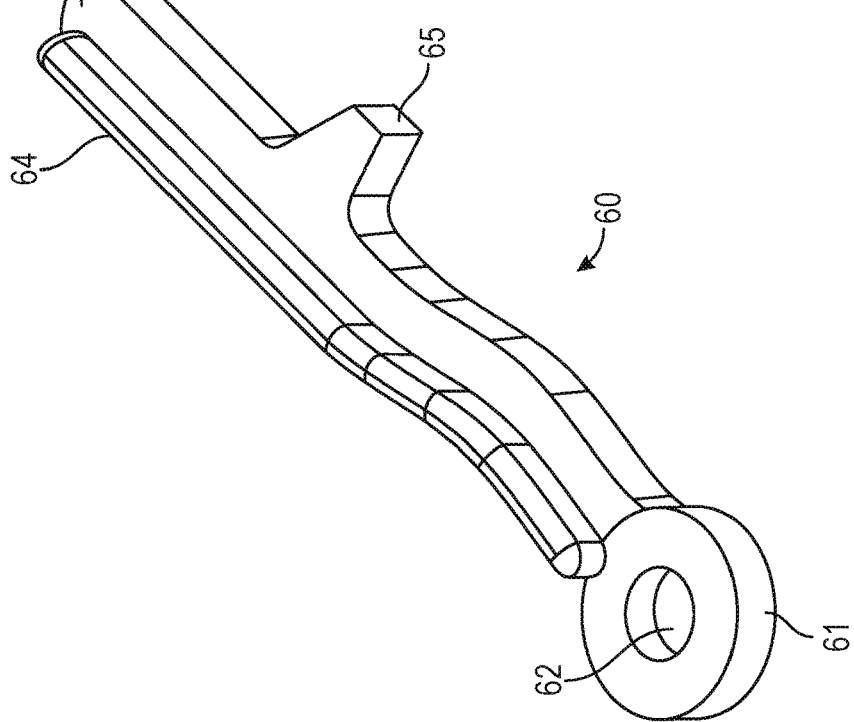
FIG. 48 shows a top perspective view of the locking member used in the lancet device shown in FIG. 1.

With reference to FIGS. 48 and 49, it can be seen that the locking member 60 includes a rear end 61 having an opening 62 which receives therein projection 10B10 and a forward end 63. An upstanding elongated projection 64 is configured to slidably engage with recess 57 of the slide 50. Such engagement causes pivoting movement of the end 63 about opening 62 between a position wherein the projection 65 locks with projection 78 (see FIG. 10) and an initial position wherein the projection 65 does not contact projection 78. An opposite facing surface to surface 63 is configured to slidably engage with a generally planar surface 10B11 (see FIG. 11). As is apparent from FIGS. 48 and 49, the locking member 60 can preferably be a one-piece member and is most preferably a one-piece synthetic resin member. Of course, the member 60 can also be an assembly of plural components provided it functions in a manner similar to that of the member shown in FIGS. 48 and 49.

One or more of the parts of the lancet device LD such as, e.g., the housing 10 and front cap 20 can preferably made transparent and/or translucent so that a user will clearly be able to see internal components. The device can also utilize one or more features or modifications disclosed in US 2006/0173478 to SCHRAGA, the disclosure of which is hereby expressly incorporated by reference in its entirety.

All the parts of the lancet device LD, with the exception of the springs and needles (which can respectively be made of spring steel and stainless steel), may be made from plastic materials and can be formed using conventional injection molding techniques or other known manufacturing methods. Bay way of non-limiting example, all or most of the parts such as the housing, trigger, front and back caps, thumb wheel, advance button, slide plate, lancet engaging member, locking member can be made of ABS plastic with the exception of the springs (which can be stainless steel) and the lancet holding member which can be made of polyoxymethylene (Delrin plastic). However, when practical, other materials and manufacturing processes may also be utilized.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A lancet device comprising:
   a housing;
   a removable front cap mounted to the housing;
   a lancet holding member extending along a longitudinal axis of the housing, the lancet holding member comprising a front section having a front end that receives therein a removable lancet, a midsection and a rear section;
   a releasable arming system comprising a trigger in communication with the front section of the lancet holding member, the trigger structured and arranged to hold the lancet holding member in a trigger-set or armed position;
   a lancet penetration depth adjustment system comprising a cam surface that engages with the lancet holding member to limit axial movement of the lancet holding member to a corresponding puncturing position;
   a lancet ejection system located closer to a front end of the housing than to a rear end of the housing and adjacent to the front section of the lancet holding member, said lancet ejection system comprising a slide member, wherein the slide member comprises:
   a lancet remover portion at a front edge of the slide member that removes or ejects the removable lancet from the lancet holding member by contact of a front edge of the slide member with a back end of the removable lancet loaded in the lancet holding member;
   a rear projection; and
   a slide button manually activatable by a user; and a plurality of springs comprising:
   a first spring that interfaces with the midsection of the lancet holding member, the first spring configured to cause movement of the lancet holding member towards the corresponding puncturing position when released from the trigger-set or armed position;
   a second spring that interfaces with the rear section of the lancet holding member, the second spring configured to cause a back cap to move towards an initial position from a retracted position; and
   a third spring configured to contact the rear projection to cause the slide member of the lancet ejection system to move towards an initial position from an extended position when the slide button is manually activated by the user, thereby providing removal of the removable lancet from the lancet holding member.

2. The lancet device of claim 1, wherein the lancet penetration depth adjustment system comprises a member having a plurality of selectable cam surfaces associated with different lancet penetration depths, where the member is at least partially rotatably mounted for selection of the cam surface from the plurality of selectable cam surfaces to limit the axial movement of the lancet holding member to the corresponding puncturing position.

3. The lancet device of claim 2, wherein the member is a thumbwheel with indicia, the thumbwheel having a rotational axis substantially perpendicular to the longitudinal axis of the housing.

4. The lancet device of claim 3, wherein the indicia is visible through an opening located in the housing.

5. The lancet device of claim 3, wherein the thumbwheel is mounted within the housing, and comprises one of:
   portions which can be gripped by the user from outside of the housing, and
   oppositely arranged portions which project outside of the housing.

6. The lancet device of claim 3, wherein each of the plurality of selectable cam surfaces are located at a different radial distance from the rotational axis of the thumbwheel.

7. The lancet device of claim 2, wherein the lancet penetration depth adjustment system comprises a thumb wheel that is frictionally engageable with a user's fingers.

8. The lancet device of claim 1, further comprising a movement preventer configured to engage with the lancet holding member as the slide button is manually activated by the user to prevent axial movement of the lancet holding member during lancet ejection.

9. The lancet device of claim 8, wherein the slide member comprises a through slot movably engaged with a guide projection extending along a portion of the movement preventer, where movement of the slide member repositions the movement preventer to restrict axial movement of the lancet holding member.

10. The lancet device of claim 1, wherein the removable front cap has an outer tapered generally circular surface, a rear end, and a generally planar front surface.

11. The lancet device of claim 1, wherein the removable front cap is removably secured to the housing via engagement between oppositely arranged projections on an interior of the removable front cap and grooves on the outer surface of the housing.

12. The lancet device of claim 1, wherein the housing comprises a retaining groove extending substantially parallel to the longitudinal axis of the housing, the third spring positioned within the retaining groove.

13. The lancet device of claim 1, wherein the first spring is positioned within the midsection of the lancet holding member.

14. The lancet device of claim 1, wherein the second spring is positioned within the rear section of the lancet holding member.

15. A lancet device comprising:
   a housing;
   a removable front cap mounted to the housing;
   lancet holding means for holding a removable lancet, the lancet holding means extending along a longitudinal axis of the housing, the lancet holding means comprising a front section having a front end that receives therein the removable lancet, a midsection and a rear section;
   a releasable arming system comprising a trigger in communication with the front section of the lancet holding means, the trigger structured and arranged to hold the lancet holding means in a trigger-set or armed position;
   a lancet penetration depth adjustment system comprising a cam surface that engages with the lancet holding means to limit axial movement of the lancet holding means to a corresponding puncturing position;
   a lancet ejection system located closer to a front end of the housing than to a rear end of the housing and adjacent to the front section of the lancet holding means, said lancet ejection system comprising a slide member, wherein the slide member comprises:
   a lancet remover portion at a front end of the slide member that removes or ejects the removable lancet from the lancet holding means by contact of a front edge of the slide member with a back end of the removable lancet loaded in the lancet holding means;
a rear projection; and
a slide button manually activatable by a user; and
a plurality of springs comprising:
   a first spring that interfaces with the midsection of the lancet holding means, the first spring configured to cause movement of the lancet holding means towards the corresponding puncturing position when released from the trigger-set or armed position;
   a second spring that interfaces with the rear section of the lancet holding means, the second spring configured to cause a back cap to move towards an initial position from a retracted position; and
   a third spring configured to contact the rear projection to cause the slide member of the lancet ejection system to move towards an initial position from an extended position when the slide button is manually activated by the user, thereby providing removal of the removable lancet from the lancet holding means.

16. The lancet device of claim 15, further comprising movement preventer means for engaging with the lancet holding means as the slide button is manually activated by the user to prevent axial movement of the lancet holding means during lancet ejection.

* * * * *